United States Patent
Amaudrut et al.

(10) Patent No.: US 8,546,385 B2
(45) Date of Patent: Oct. 1, 2013

(54) BENZOIC PYRROLOPYRIDINE DERIVATIVES

(75) Inventors: Jerome Amaudrut, Dijon (FR); Benaissa Boubia, Saint Apollinaire (FR); Fabrice Guillier, Belleneuve (FR); Olivia Poupardin-Olivier, Varois et Chaignot (FR)

(73) Assignee: Laboratoires FOURNIER SA, Dijon (FR)

( * ) Notice: Subject to any disclaimer, the term of this patent is extended or adjusted under 35 U.S.C. 154(b) by 0 days.

(21) Appl. No.: 13/519,774

(22) PCT Filed: Jan. 7, 2011

(86) PCT No.: PCT/FR2011/050023
§ 371 (c)(1), (2), (4) Date: Jun. 28, 2012

(87) PCT Pub. No.: WO2011/083278
PCT Pub. Date: Jul. 14, 2011

(65) Prior Publication Data
US 2012/0302560 A1 Nov. 29, 2012

(30) Foreign Application Priority Data
Jan. 8, 2010 (FR) ...................................... 10 50113

(51) Int. Cl.
| | |
|---|---|
| A61K 31/437 | (2006.01) |
| A61K 31/538 | (2006.01) |
| A61P 25/16 | (2006.01) |
| A61P 25/28 | (2006.01) |
| C07D 471/04 | (2006.01) |

(52) U.S. Cl.
USPC ......... 514/230.5; 514/300; 544/105; 546/112

(58) Field of Classification Search
None
See application file for complete search history.

(56) References Cited

U.S. PATENT DOCUMENTS

| | | |
|---|---|---|
| 7,087,756 B2 | 8/2006 | Hintermann et al. |
| 7,704,989 B2 | 4/2010 | El-Ahmad et al. |
| 7,902,219 B2 | 3/2011 | Peyronel et al. |
| 2008/0200495 A1* | 8/2008 | Boubia et al. ................. 514/300 |
| 2009/0143421 A1 | 6/2009 | Peyronel |

FOREIGN PATENT DOCUMENTS

| | | |
|---|---|---|
| FR | 2 903 105 A1 | 1/2008 |
| FR | 2 903 106 A1 | 1/2008 |
| FR | 2 903 107 A1 | 1/2008 |
| WO | WO 98/25611 A1 | 6/1998 |
| WO | WO 03/015780 A2 | 2/2003 |
| WO | WO 2005/009958 A1 | 2/2005 |
| WO | WO 2005/047268 A2 | 5/2005 |
| WO | WO 2008/101247 A2 | 8/2008 |
| WO | WO 2010/002802 A1 | 1/2010 |

OTHER PUBLICATIONS

Rolf Zetterstroem et al., "Dopamine Neuron Agenesis in Nurr1-Deficient Mice", vol. 276, 1997, (four (4) pages).
Christopher A. Lipinski, "Bioisosterism in Drug Design", 1986, vol. 21, pp. 283-291.
Janet E. Graham et al., "Theoretical Studies Applied to Drug Design: Ab Initio Electronic Distributions in Bioisosteres", Theo Chem, Journal of Molecular Structure, (1995), vol. 343, pp. 105-109.
Asa Wallen-Mackenzie et al., "Nurr1-RXR Heterodimers Mediate RXR Ligand-Induced Signaling in Neuronal Cells", Genes & Development, vol. 17, pp. 3036-3047.

* cited by examiner

*Primary Examiner* — Janet Andres
*Assistant Examiner* — Timothy R Rozof
(74) *Attorney, Agent, or Firm* — Crowell & Moring LLP

(57) ABSTRACT

The present invention relates to compounds of formula:

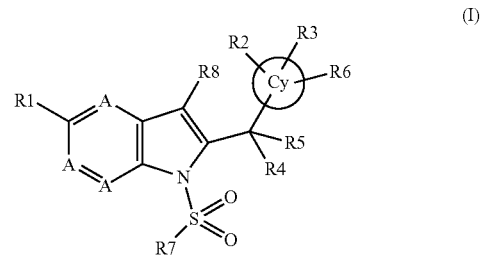

(I)

in which A, Cy, R1, R2, R3, R4, R5, R6, R7 and R8 are as defined in the description.
The compounds of the invention are modulators of the NURR-1 nuclear receptors.

21 Claims, No Drawings

BENZOIC PYRROLOPYRIDINE DERIVATIVES

The present invention relates to novel compounds of pyrrolopyridine type, preferentially derivatives of benzoic pyrrolopyridine type, and also to the process for preparing them and to their use as active principles of medicaments, especially for treating and/or preventing diseases involving the NURR-1 nuclear receptors. More specifically, this invention relates to the use of these compounds for the manufacture of a medicament for treating and/or preventing neurodegenerative diseases and in particular Parkinson's disease.

PRIOR ART

Neurodegenerative diseases are defined as diseases characterized by progressive dysfunction of the nervous system. They are often associated with atrophy of the affected structures of the central or peripheral nervous system. They include, inter alia, diseases such as Alzheimer's disease, Creutzfeldt-Jakob disease, Huntington's disease, Parkinson's disease, lysosomal diseases, progressive supranuclear paralysis, multiple sclerosis and amyotrophic lateral sclerosis. Among these neurodegenerative diseases, Parkinson's disease is a complaint that affects about four million people worldwide. Although it affects individuals of all ages, it is more common among the elderly (with 2% of people over the age of 65 affected by this disease). It is characterized by neurodegeneration of the dopaminergic neurons of the substantia nigra. These types of neuron synthesize dopamine and use it as a neurotransmitter.

A relationship has been able to be established between dopamine deficiency and nervous disorders. Dopamine exerts a central role in controlling voluntary movements, cognitive functions and the development of emotion-related behaviour.

The current therapeutic strategy for treating Parkinson's disease is based on attenuating the symptoms, by compensating for the dopamine deficiency via the administration of a metabolic precursor such as L-DOPA.

However, presently, the increase in prevalence of this pathology has made it necessary to develop novel therapeutic agents that exert a beneficial role in neuronal survival and differentiation.

This development has led to the identification of compounds that are capable of activating the nuclear receptors involved in the pathogenesis of Parkinson's disease.

The transcription factor NURR-1, a member of the superfamily of orphan nuclear receptors, which is strongly expressed in the brain, was identified as having an essential role in the development and maintenance of the dopaminergic neurons of the mesencephalon (Zetterstrom et al. 1997, Science 276 (5310): 248-50).

The NURR-1 nuclear receptor is involved in maintaining the dopaminergic phenotype via regulation of the specific genes of the dopaminergic neurons (DA). It also promotes the survival of the DA neurons by protecting them against toxic attack. The NURR-1 nuclear receptor thus serves as a specific transcription factor for the dopaminergic neurons, the activities of which might be regulated by modulating the dopaminergic neurotransmission in Parkinson's disease.

This receptor binds to DNA in the form of monomers, homodimers or heterodimers with RXR (retinoid X receptor), a nuclear receptor that is the heteropartner of many other members of the family of nuclear receptors. RXR is involved in many physiological processes, such as fat and glucose metabolism, development and differentiation. NURR-1 thus interacts with the α and γ isoforms of RXR. RXRα is ubiquitously expressed, whereas the expression of RXRγ is concentrated mainly in the brain and especially in the striatum, the hypothalamus and the pituitary.

The formed complexes NURR-1/RXRα and NURR-1/RXRγ are capable of regulating transcription in response to an RXR ligand. RXR thus positively modulates the transcription activation potential of NURR-1.

The identification of compounds capable of inducing the activity of the NURR-1/RXRα and NURR-1/RXRγ complexes should consequently make it possible to provide novel routes for treating Parkinson's disease.

Document WO 2003/015 780 discloses heterocyclic compounds that are active for treating Parkinson's disease. Heterocyclic compounds with affinity for the PPAR receptors are described in document WO 2005/009 958.

Moreover, documents FR 2 903 105, FR 2 903 106 and FR 2 903 107 describe compounds that are activators of the NURR-1 receptor, while the use of heterocyclic compounds that modulate the activity of receptors of the NGFI-B family (of which NURR-1 is a member) is described in document WO 2005/047 268.

Heterocyclic compounds presented as being factor Xa inhibitors are described in document WO 98/25611. Other heterocyclic compounds presented as 5-HT6 receptor modulators are described in documents WO 2008/101 247 and WO 2010/002 802.

The following 1H-pyrrolo[2,3-b]pyridine derivatives are described in document: Tetrahedron, vol. 53, No. 10, pp. 3637-3648, 1997:
  2-[[1-(phenylsulfonyl)-1H-pyrrolo[2,3-b]pyridin-2-yl]carbonyl]benzoic acid;
  N,N-diethyl-4-[hydroxy[1-(phenylsulfonyl)-1H-pyrrolo[2,3-b]pyridin-2-yl]methyl]-2-methoxy-3-pyridinecarboxamide;
  N,N-diethyl-2-methoxy-4-[[1-(phenylsulfonyl)-1H-pyrrolo[2,3-b]pyridin-2-yl]carbonyl]-3-pyridinecarboxamide;
  N,N-diethyl-4-[1-hydroxy-1-[1-(phenylsulfonyl)-1H-pyrrolo[2,3-b]pyridin-2-yl]ethyl]-2-methoxy-3-pyridinecarboxamide.

These compounds are intermediates in the synthesis of polyazatetracyclic compounds.

SUBJECT OF THE INVENTION

According to a first aspect, the present invention relates to novel compounds of pyrrolopyridine type that are NURR-1/RXRα and NURR-1/RXRγ agonists, capable of inhibiting the neuronal degeneration observed in Parkinson's disease, chosen from:
(i) the compounds of formula (I):

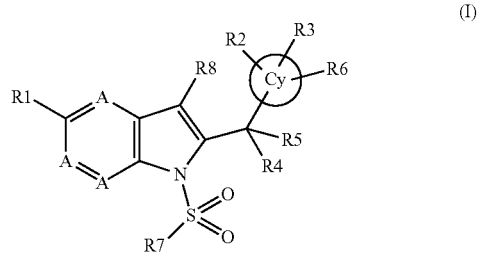

in which:
  one of the groups A represents a nitrogen atom and the other groups A represent a carbon atom;
  Cy represents a phenyl or a 5- or 6-membered heteroaromatic ring;
  R1 represents a hydrogen atom, a halogen atom, a group $(C_1-C_4)$alkyl that is optionally totally or partially halogenated, or a group $(C_1-C_4)$alkoxy;

R2 and R3 represent, independently of each other, a hydrogen atom, a halogen atom, a group $(C_1-C_4)$alkyl, a hydroxyl group or a group $(C_1-C_4)$alkoxy;

R4 and R5 represent, independently of each other, a hydrogen atom, a halogen atom, a group $(C_1-C_4)$alkyl or a hydroxyl group;

or R4 and R5 form, together with the carbon atoms to which they are attached, an ethylene group (C=CH$_2$) or a carbonyl group (C=O);

R6 represents a group —COOR9 or a carboxylic acid bioisostere group, preferably a group —COOR9;

R7 represents a phenyl optionally substituted with a group $(C_1-C_4)$alkyl, or a 6- to 10-membered heteroaromatic ring optionally substituted with a group $(C_1-C_4)$alkyl;

R8 represents a hydrogen atom, a group $(C_1-C_4)$alkyl or a halogen atom;

R9 represents a hydrogen atom or a group $(C_1-C_4)$alkyl; and (ii) the pharmaceutically acceptable salts of the said compounds of formula (I).

According to a second aspect, the invention relates to the above-mentioned compounds for their use as therapeutically active substances, especially in the treatment and/or prevention of neurodegenerative diseases, in particular Parkinson's disease, and also to pharmaceutical compositions containing them.

According to a third aspect, the invention relates to the use of at least one compound of formula (I), or a pharmaceutically acceptable salt thereof, as an active principle for the preparation of a medicament for treating diseases in which the NURR-1 receptor is involved, especially neurodegeneration, in particular such as Parkinson's disease.

According to a fourth aspect, the invention relates to a method for preventing and/or treating diseases in which the NURR-1 receptor is involved, especially neurodegenerative diseases, and more particularly Parkinson's disease, which consists in administering to a patient in need thereof a therapeutically effective amount of a compound of formula (I) or a pharmaceutically acceptable salt of the said compound, or a pharmaceutical composition containing such a compound.

DETAILED DESCRIPTION

The term "alkyl group" means a saturated hydrocarbon-based chain which may be linear or branched. For example, and without limitation, an alkyl group containing from 1 to 6 carbon atoms may be a methyl, ethyl, propyl, butyl, pentyl, hexyl, 1-methylethyl, 1-methylpropyl, 2-methylpropyl, 1,1-dimethylethyl, 1-methylbutyl, 1,1-dimethylpropyl, 1-methylpentyl or 1,1-dimethylbutyl group.

The term "halogen" means a bromine, fluorine or chlorine atom.

The term "partially or totally halogenated alkyl group" means an alkyl group as defined above in which one or more hydrogen atoms are replaced with one or more halogen atoms. Examples that may be mentioned include difluoromethyl and trifluoromethyl groups.

The term "alkoxy group" means a group OR in which R is an alkyl group as defined above. Examples of alkoxy groups containing from 1 to 4 carbon atoms that may be mentioned include methoxy, ethoxy, propoxy, butoxy, 1-methylethoxy, 1,1-dimethylethoxy, 1-methylpropoxy and 2-methylpropoxy groups.

The term "5- or 6-membered heteroaromatic ring" means an aromatic monocycle comprising from 1 to 3 heteroatoms and preferably 1 or 2 heteroatoms, chosen from nitrogen, oxygen and sulfur. Examples that may be mentioned include pyrrolyl, pyrazolyl, imidazolyl, oxazolyl, isoxazolyl, triazolyl, oxadiazolyl, furyl, thienyl thiazolyl, isothiazolyl, thiadiazolyl, pyridyl, pyridazinyl, pyrimidinyl, pyrazinyl and triazinyl groups.

The term "6- to 10-membered heteroaromatic ring" means an unsaturated or partially unsaturated monocyclic or bicyclic group comprising from 1 to 4 heteroatoms, preferably from 1 to 3 heteroatoms and more preferably 1 or 2 heteroatoms, chosen from nitrogen, oxygen and sulfur, the said group being optionally substituted with a $(C_1-C_4)$alkyl. Examples that may be mentioned include pyridyl, pyridazinyl, pyrimidinyl, pyrazinyl, triazinyl, 1,2,3,4-isoquinolinyl, quinolinyl, 1,2,3,4-tetrahydroquinolinyl, benzimidazolyl, benzopyrazinyl, indolyl, 2,3-dihydroindolyl, benzofuryl, 2,3-dihydrobenzofuryl, benzothiazolyl, benzothiadiazolyl, benzisoxazolyl, 3,4-dihydro-1,4-benzoxazinyl, 1,3-benzodioxolyl, 2,3-dihydrobenzodioxinyl, imidazothiazolyl and benzoxazolyl groups.

The term "carboxylic acid bioisostere group" means a group with chemical and physical similarities and that produces biological properties broadly similar to a carboxylic group, as described in Lipinski, Annual Reports in Medicinal Chemistry, 1986, 21, p. 283 "Bioisosterism In Drug Design"; Graham, Theochem., 1995, 343, pp. 105-109 "Theoretical Studies Applied To Drug Design: ab initio Electronic Distributions In Bioisosteres".

Examples of carboxylic acid bioisostere groups that may be mentioned include optionally substituted acylhydrazine groups, optionally substituted acylhydrazine carboxylates, optionally substituted alkyl and aryl sulfonylcarbamoyls, carboxamides, optionally substituted sulfonamides, oxadiazolones, optionally substituted phosphonates, optionally substituted isothiazoles, optionally substituted isoxazoles, optionally substituted isoxazolones, tetrazoles, optionally substituted thiazolidinediones and optionally substituted thioxothiazolidinones. Advantageously, the carboxylic acid bioisostere group is chosen from the groups —SO$_2$NHR10, —CONHNHCOOR11, —CONR12R13 and —CONHSO$_2$R14, in which R10, R11, R12, R13 and R14 represent, independently of each other, a hydrogen atom or a group $(C_1-C_4)$alkyl, and preferably from the groups —CONR12R13 and —CONHSO$_2$R14. The carboxylic acid bioisostere group may also be chosen from the groups

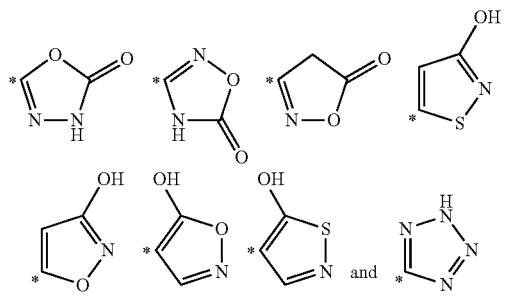

in which the symbol * denotes the point of attachment to the ring Cy.

The compounds of formula (I) in which the substituents R4 and R5 are different have an asymmetric centre. For these compounds, the invention covers both the racemic compound and each of the optical isomers considered separately.

The compounds of formula (I) in which R6 represents a group COOH are carboxylic acids that may be used in the form of free acids or in the form of salts, the said salts being obtained by combining the acid with a non-toxic and preferably pharmaceutically acceptable mineral or organic base. Among the mineral bases, use may be made, for example, of sodium, potassium, magnesium or calcium hydroxide. Among the organic bases, use may be made, for example, of amines, amino alcohols, basic amino acids such as lysine or arginine, or alternatively compounds bearing a quaternary ammonium function, for instance betaine or choline. The salts of the acids of formula (I) with a mineral or organic base may be obtained conventionally by using the methods that are well known to those skilled in the art, for example by mixing stoichiometric amounts of the acid of formula (I) in which R6=COOH and of the base in a solvent, for instance water or an aqueous-alcoholic mixture, and then freeze-drying the solution obtained.

According to one embodiment of the invention, the said invention concerns the compounds of formula (I) with the exception of the following compounds:

2-[[1-(phenylsulfonyl)-1H-pyrrolo[2,3-b]pyridin-2-yl]carbonyl]benzoic acid;

N,N-diethyl-4-[hydroxy[1-(phenylsulfonyl)-1'-1-pyrrolo[2,3-b]pyridin-2-yl]methyl]-2-methoxy-3-pyridine carboxamide;

N,N-diethyl-2-methoxy-4-[[1-(phenylsulfonyl)-1,4-pyrrolo[2,3-b]pyridin-2-yl]carbonyl]-3-pyridinecarboxamide;

N,N-diethyl-4-[1-hydroxy-1-[1-(phenylsulfonyl)-1H-pyrrolo[2,3-b]pyridin-2-yl]ethyl]-2-methoxy-3-pyridinecarboxamide.

A preferred family of compounds according to the invention corresponds to formula (I) in which R1 represents a halogen atom or a totally or partially halogenated group ($C_1$-$C_4$)alkyl and/or R8 represents a hydrogen atom.

Another preferred family of compounds according to the invention corresponds to formula (I) in which:

Cy represents a phenyl or a 5- or 6-membered heteroaromatic ring;

R1 represents a halogen atom or an optionally totally or partially halogenated group ($C_1$-$C_4$)alkyl;

R2 and R3 represent, independently of each other, a hydrogen atom or a halogen atom;

R4 and R5 represent, independently of each other, a hydrogen atom, a halogen atom or a hydroxyl group, or R4 and R5 form, together with the carbon atom to which they are attached, a carbonyl group (C=O);

R6 represents a group —COOR9;

R7 represents a phenyl optionally substituted with a group ($C_1$-$C_4$)alkyl;

R8 represents a hydrogen atom;

R9 represents a hydrogen atom or a group ($C_1$-$C_4$)alkyl.

Among this family, the preferred compounds are those of formula (I) in which R4 and R5 represent, independently of each other, a hydrogen atom or a hydroxyl group.

Among the compounds described above, the ones that are preferred are those that satisfy at least one of the following conditions:

Cy represents a phenyl, thienyl, thiazolyl, furyl or pyridyl, preferably a phenyl or a thienyl;

R2 and R3 each represent a hydrogen atom;

R4 and R5 each represent a hydrogen atom.

As compounds that are most particularly preferred, mention may be made of:

5-[[1-[[3-(1,1-dimethylethyl)phenyl]sulfonyl]-5-(trifluoromethyl)-1H-pyrrolo[3,2-b]pyridin-2-yl]methyl]-thiophene-2-carboxylic acid, 3-[[1-[[3-(1,1-dimethylethyl)phenyl]sulfonyl]-5-(trifluoromethyl)-1H-pyrrolo[2,3-c]pyridin-2-yl]methyl]-2-benzoic acid, 2-chloro-4-[[1-[[3-(1,1-dimethylethyl)phenyl]sulfonyl]-5-(trifluoromethyl)-1H-pyrrolo[2,3-c]pyridin-2-yl]methyl]-benzoic acid, 5-[[1-[[3-(1,1-dimethylethyl)phenyl]sulfonyl]-5-(trifluoromethyl)-1H-pyrrolo[2,3-c]pyridin-2-yl]methyl]-furane-3-carboxylic acid, 5-[[1-[[3-(1,1-dimethylethyl)phenyl]sulfonyl]-5-(trifluoromethyl)-1H-pyrrolo[2,3-c]pyridin-2-yl]methyl]-pyridine-3-carboxylic acid, 4-[[1-[[3-(1,1-dimethylethyl)phenyl]sulfonyl]-5-(trifluoromethyl)-1H-pyrrolo[2,3-c]pyridin-2-yl]methyl]-thiophene-2-carboxylic acid, 5-[[1-[[3-(1,1-dimethylethyl)phenyl]sulfonyl]-5-(trifluoromethyl)-1H-pyrrolo[2,3-c]pyridin-2-yl]methyl]-2-fluoro-benzoic acid, 2-[[1-[[3-(1,1-dimethylethyl)phenyl]sulfonyl]-5-(trifluoromethyl)-1H-pyrrolo[3,2-b]pyridin-2-yl]methyl]-thiazole-4-carboxylic acid, Methyl 4-[1-(4-(1-methylethyl)phenylsulfonyl)-5-trifluoromethyl-1H-pyrrolo[2,3-b]pyridin-2-ylmethyl]-benzoate, 4-[[1-[[3-(1-methylethyl)phenyl]sulfonyl]-5-(trifluoromethyl)-1H-pyrrolo[2,3-b]pyridin-2-yl]methyl]-benzoic acid, Methyl 4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]-benzoate, 4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]-benzoic acid, Methyl 4-[1-(4-(1-methylethyl)phenylsulfonyl)-5-trifluoromethyl-1H-pyrrolo[2,3-c]pyridin-2-ylmethyl]-benzoate, 4-[[1-[[4-(1-methylethyl)phenyl]sulfonyl]-5-(trifluoromethyl)-1H-pyrrolo[2,3-c]pyridin-2-yl]methyl]-benzoic acid, Methyl 4-[1-(4-(1-methylethyl)phenylsulfonyl)-5-trifluoromethyl-1H-pyrrolo[3,2-b]pyridin-2-ylmethyl]-benzoate, 4-[1-(4-(1-methylethyl)phenylsulfonyl)-5-trifluoromethyl-1H-pyrrolo[3,2-b]pyridin-2-ylmethyl]-benzoic acid, Methyl 4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]-benzoate, 4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]-benzoic acid, Methyl 4-[1-(4-(1-methylethyl)phenylsulfonyl)-5-chloro-1H-pyrrolo[2,3-e]pyridin-2-ylmethyl]-benzoate, 4-[[5-chloro-1-[[4-(1-methylethyl)phenyl]sulfonyl]-1H-pyrrolo[2,3-c]pyridin-2-yl]methyl]-benzoic acid, Methyl 4-[1-(3-(1,1-dimethylethyl)phenylsulfonyl)-5-trifluoromethyl-1H-pyrrolo[3,2-b]pyridin-2-ylmethyl]-benzoate, 4-[[1-[[3-(1,1-dimethylethyl)phenyl]sulfonyl]-5-(trifluoromethyl)-1H-pyrrolo[3,2-b]pyridin-2-yl]methyl]-benzoic acid, Methyl 4-{Hydroxy-[1-(3-(1-methylethyl)phenylsulfonyl)-5-trifluoromethyl-1H-pyrrolo[2,3-b]pyridin-2-yl]-methyl}-benzoate, Methyl 4-[1-(3-(1-methylethyl)phenylsulfonyl)-5-trifluoromethyl-1H-pyrrolo[2,3-b]pyridin-2-ylmethyl]-benzoate, 4-[[1-[[3-(1-methylethyl)phenyl]sulfonyl]-5-(trifluoromethyl)-1H-pyrrolo[2,3-b]pyridin-2-yl]methyl]-benzoic acid, Methyl 4-{Hydroxy-[1-(3-(1,1-dimethylethyl)phenylsulfonyl)-5-trifluoromethyl-1H-pyrrolo[2,3-b]pyridin-2-yl]-methyl}-benzoate, Methyl 4-[1-(3-(1,1-dimethylethyl)phenylsulfonyl)-5-trifluoromethyl-1H-pyrrolo[2,3-b]pyridin-2-ylmethyl]-benzoate, 4-[[1-[[3-(1,1-dimethylethyl)phenyl]sulfonyl]-5-(trifluoromethyl)-1H-pyrrolo[2,3-b]pyridin-2-yl]methyl]-benzoic acid, Methyl 4-{Hydroxy-[5-chloro-1-(4-(1-methylethyl)phenylsulfonyl)-1H-pyrrolo[2,3-b]pyridin-2-yl]-methyl}-benzoate, Methyl 4-[5-Chloro-1-(4-(1-methylethyl)phenylsulfonyl)-1H-pyrrolo[2,3-b]pyridin-2-ylmethyl]-benzoate, 4-[[5-chloro-1-[[4-(1-methylethyl)phenyl]sulfonyl]-1H-pyrrolo-[2,3-b]pyridin-2-yl]methyl]-benzoic acid, 5-{hydroxy[1-(3-(1,1-dimethylethyl)phenylsulfonyl)-5-trifluoromethyl-1H-pyrrolo[3,2-b]pyridin-2-yl]methyl}thiophene-2-carboxylic acid, 5-[[1-[[3-(1,1-dimethylethyl)phenyl]sulfonyl]-5-(trifluoromethyl)-1H-pyrrolo[3,2-b]pyridin-2-yl]fluoromethyl]-N,N-diethyl-2-thiophenecarboxamide, 5-{1-(3-(1,1-dimethylethyl)phenylsulfonyl)-5-trifluoromethyl-1H-pyrrolo[3,2-b]pyridine-2-carbonyl}thiophene-2-carboxylic acid, 4-[[5-chloro-1-[[4-(1-methylethyl)phenyl]sulfonyl]-1H-pyrrolo[2,3-b]pyridin-2-yl]methyl]benzoic acid, sodium salt, 4-[[5-chloro-1-[[4-(1-methylethyl)phenyl]sulfonyl]-1H-pyrrolo[2,3-b]pyridin-2-yl]methyl]benzoic acid, piperazine salt, 4-[[1-[[3-(1,1-dimethylethyl)phenyl]sulfonyl]-3-methyl-5-(trifluoromethyl)-1H-pyrrolo[3,2-b]pyridin-2-yl]methyl]-benzoic acid, 5-[[1-[[4-(1,1-methylethyl)phenyl]sulfonyl]-5-chloro-1H-pyrrolo[2,3-b]pyridin-2-yl]methyl]thiophene-2-carboxylic acid, N-{4-[1-(3-tert-butylbenzenesulfonyl)-5-trifluoromethyl-1H-pyrrolo[3,2-b]pyridin-2-ylmethyl]benzoyl}methanesulfonamide.

The syntheses described below, including those in the preparations and the examples, illustrate methods for preparing the compounds of formula (I). In these syntheses, the substituents A, Cy, R1, R2, R3, R4, R5, R6, R7 and R8 have the meaning indicated above for the compounds of formula (I), unless otherwise indicated.

According to a first embodiment, the compounds of formula (I) in which R4 represents H, OH or $(C_1$-$C_4)$alkyl and R5 represents H may be prepared as described in Scheme 1.

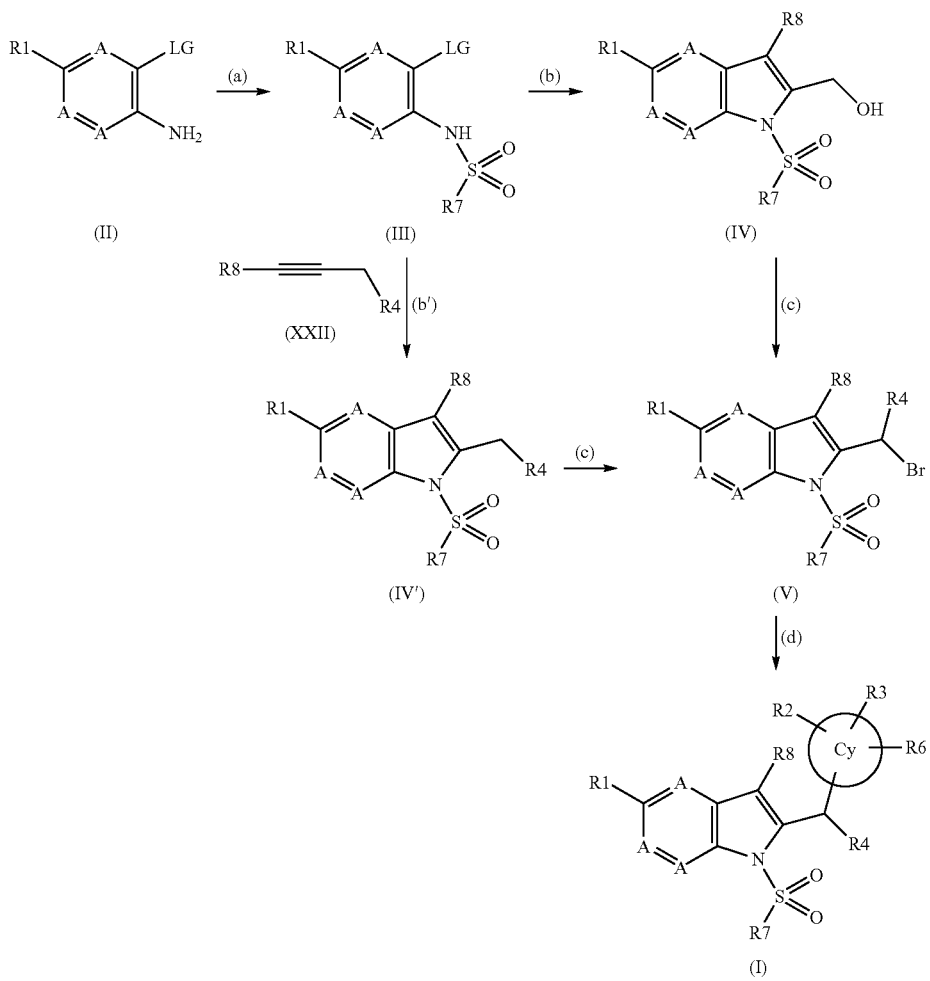

Scheme 1

LG = I, Br, Tosylate

Step (a)

An amine of formula (II), in which LG is preferably iodine, is reacted with a sulfonyl chloride R7SO₂Cl in the presence of a suitable base, for instance pyridine, at room temperature for about 2 to 24 hours. The reaction medium thus obtained is then reacted with a suitable base, for instance potassium hydroxide, in a suitable solvent, for instance dioxane, at a temperature between room temperature and the reflux temperature of the solvent, for a period of about 1 to 6 hours. The compound of formula (III) is thus obtained.

Step (b)

The compound of formula (III) is reacted with 2-propyn-1-ol in the presence of copper iodide and a palladium-based catalyst, for instance bis(triphenylphosphine)palladium(II) chloride, in a suitable solvent, for instance N,N-dimethylformamide (DMF). A suitable base is then added, for instance diethylamine or triethylamine, and the reaction mixture is heated for a period of about 1 to 6 hours at a temperature between room temperature and the reflux temperature of the solvent. According to one variant, the heating may be performed in a microwave oven for a period of about 5 to 30 minutes. The compound of formula (IV) is thus obtained where R8 represents a hydrogen atom.

Step (b')

The compound of formula (III) is reacted with an alkyne of formula (XXII) in the presence of a palladium-based catalyst, for instance palladium acetate, and lithium chloride in a suitable solvent, for instance N,N-dimethylformamide (DMF). A suitable base is then added, for instance potassium carbonate, and the reaction mixture is heated for a period of about 1 to 24 hours at a temperature between room temperature and the reflux temperature of the solvent. According to one variant, the heating may be performed in a microwave oven for a period of about 5 to 30 minutes. The compound of formula (IV') is thus obtained where R8 represents a group ($C_1$-$C_4$) alkyl, Step (c)

The compound of formula (IV) or (IV') is reacted with a source of bromine, for instance phosphorus tribromide, in a suitable solvent, for instance dichloromethane (DCM), at 0° C. or at room temperature for a period of about 1 hour to 4 days, or N-bromosuccinimide (NBS) in the presence of azobisisobutyronitrile (AIBN) in a suitable solvent, for instance refluxing carbon tetrachloride, for 24 hours. The compound of formula (V) is thus obtained.

Step (d)

The compound of formula (V) dissolved in a suitable solvent, for instance an ethanol/dioxane mixture, is reacted with a compound of formula $(HO)_2\mu$-Cy(R2,R3)-R6 in the presence of a palladium-based catalyst, for instance the complex $Pd(dppf)Cl_2 \cdot CH_2Cl_2$, and of a suitable base, for instance potassium carbonate, and the reaction mixture is heated for a period of about 1 to 6 hours at a temperature between room temperature and the reflux temperature of the solvent. According to one variant, the heating may be performed in a microwave oven for a period of about 5 to 30 minutes. The compound of formula (I) is thus obtained. If necessary (when R6=COOR9 and R9=($C_1$-$C_4$)alkyl), the ester function of the compound of formula (I) is hydrolysed, for example via the action of a mineral base such as lithium hydroxide, according to procedures that are well known to those skilled in the art, to obtain a compound of formula (I) in which R6=COOH.

According to a second embodiment, the compounds of formula (I) in which R4 and R5 represent H may be prepared as described in Scheme 2.

Scheme 2

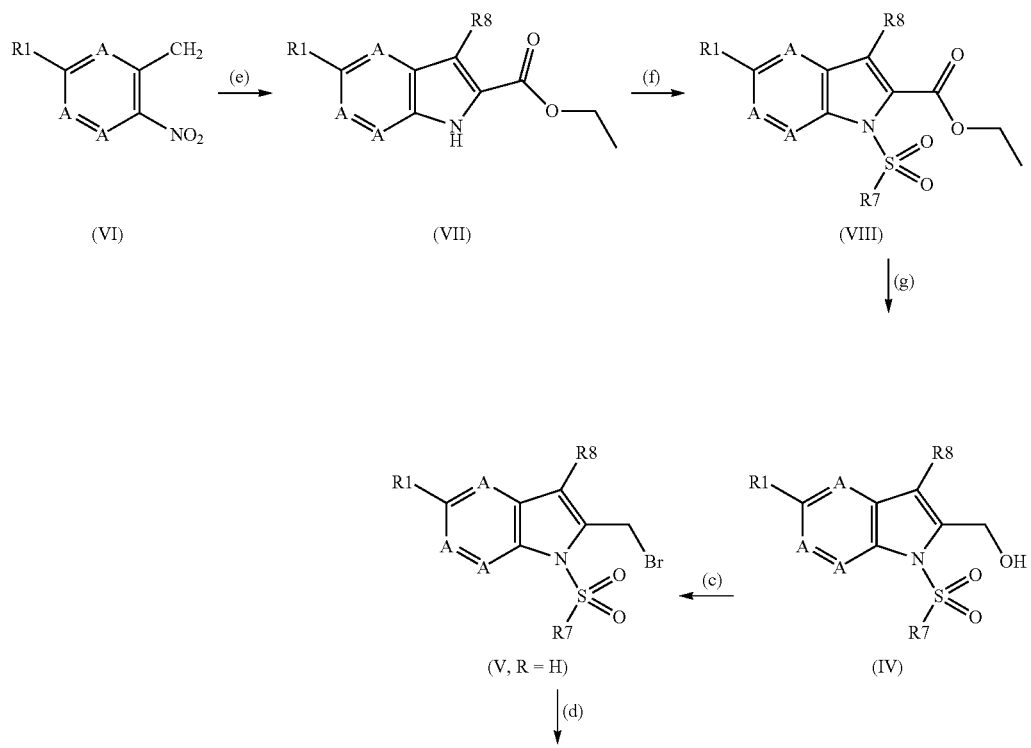

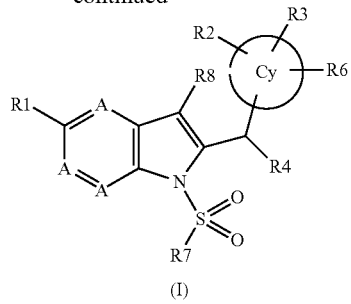

(I)

Step (e)

The compound of formula (VI) is reacted with diethyl oxalate in the presence of a suitable base, for instance 1,8-diazabicyclo[5.4.0]undec-7-ene (DBU), at room temperature, for a period of about 1 to 6 hours. If necessary, the compound obtained is reacted with a halogenating agent, for instance 1-chloromethyl-4-fluoro-1,4-diazoniabicyclo[2.2.2]octane bis(tetrafluoroborate), in a suitable solvent, for instance acetonitrile, at a temperature of between 0 and 50° C., for a period of about 1 to 96 hours. The compound of formula (VII) is thus obtained.

Step (f)

The compound of formula (VII) is treated with a suitable base, for instance sodium hydride, in a suitable solvent, for instance tetrahydrofuran (THF), at room temperature for a period of about 1 to 6 hours, and is then reacted with a sulfonyl chloride R7SO$_2$Cl at room temperature for a period of about 2 to 24 hours. The compound of formula (VIII) is thus obtained.

Step (g)

The compound of formula (VIII) is treated with a suitable reducing agent, for instance DIBAL-H or LiAlH$_4$, in a suitable solvent, for instance toluene, at a temperature of between about −78° C. and room temperature, for a period of about 1 to 24 hours. The compound of formula (IV) is thus obtained.

Step (c)

This step is identical to step (c) described for Scheme 1, and leads to the production of the compound of formula (V).

Step (d)

This step is identical to step (d) described for Scheme 1, and leads to the production of the compound of formula (I). If necessary (when R6=COOR9 and R9=(C$_1$-C$_4$)alkyl), the ester function of the compound of formula (I) is hydrolysed, for example via the action of a mineral base such as lithium hydroxide, according to procedures that are well known to those skilled in the art, to obtain a compound of formula (I) in which R6=COOH.

According to a third embodiment, the compounds of formula (I) in which R2, R3, R4, R5 and R8 represent H, Cy represents a thiazolyl and R6 represents COOH may be prepared as described in Scheme 3.

Scheme 3

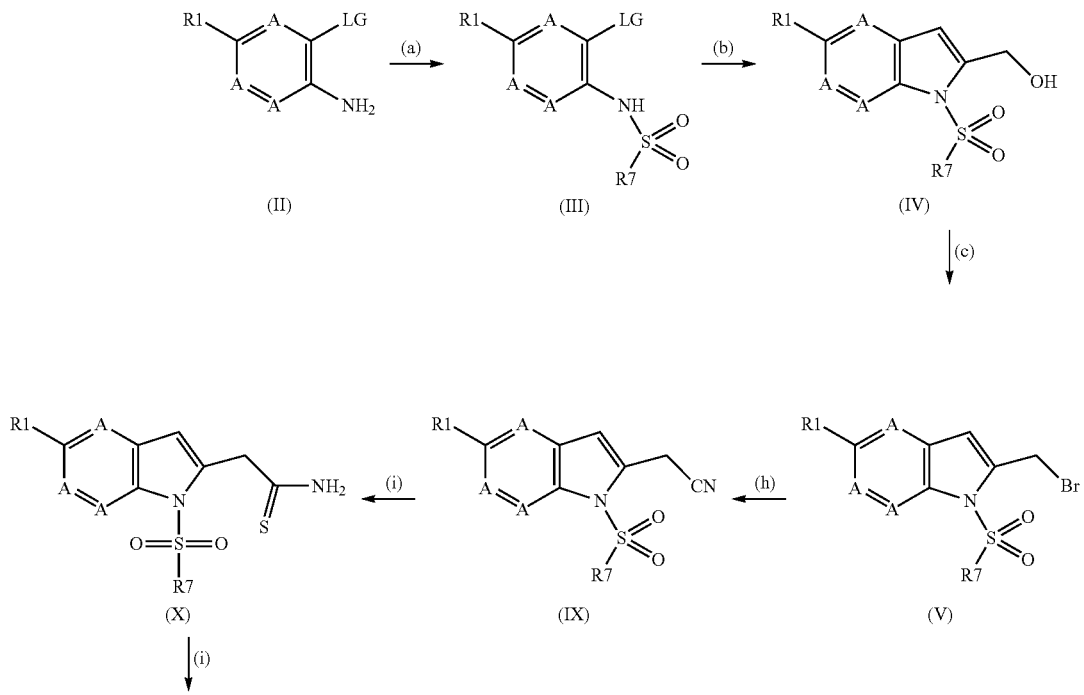

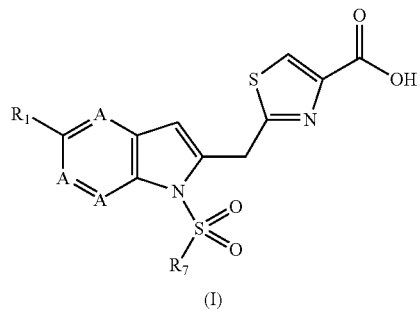

LG = I, Br, Tosylate

Step (a)

This step is identical to step (a) described for Scheme 1, and leads to the production of the compound of formula (III).

Step (b)

This step is identical to step (b) described for Scheme 1, and leads to the production of the compound of formula (IV).

Step (c)

This step is identical to step (c) described for Scheme 1, and leads to the production of the compound of formula (V).

Step (h)

The compound of formula (V) is reacted with potassium cyanide in a suitable solvent, for instance DCM, in the presence of a phase-transfer catalyst, for instance tetrabutylammonium bromide, at room temperature for a period of about 1 to 4 days. The compound of formula (IX) is thus obtained.

Step (i)

The compound of formula (IX) dissolved in a suitable solvent, for instance a THF/water mixture, is reacted with diethyl dithiophosphate at a temperature of about 80 to 120° C. for a period of about 1 to 6 hours. The compound of formula (X) is thus obtained.

Step (j)

The compound of formula (X) is reacted with bromopyruvic acid in a suitable solvent, for instance ethanol, at room temperature for a period of about 12 to 36 hours. The compound of formula (I) is thus obtained.

According to a fourth embodiment, the compounds of formula (I) in which R4 and R8 represent H and Cy represents a phenyl may be prepared as described in Scheme 4.

Scheme 4

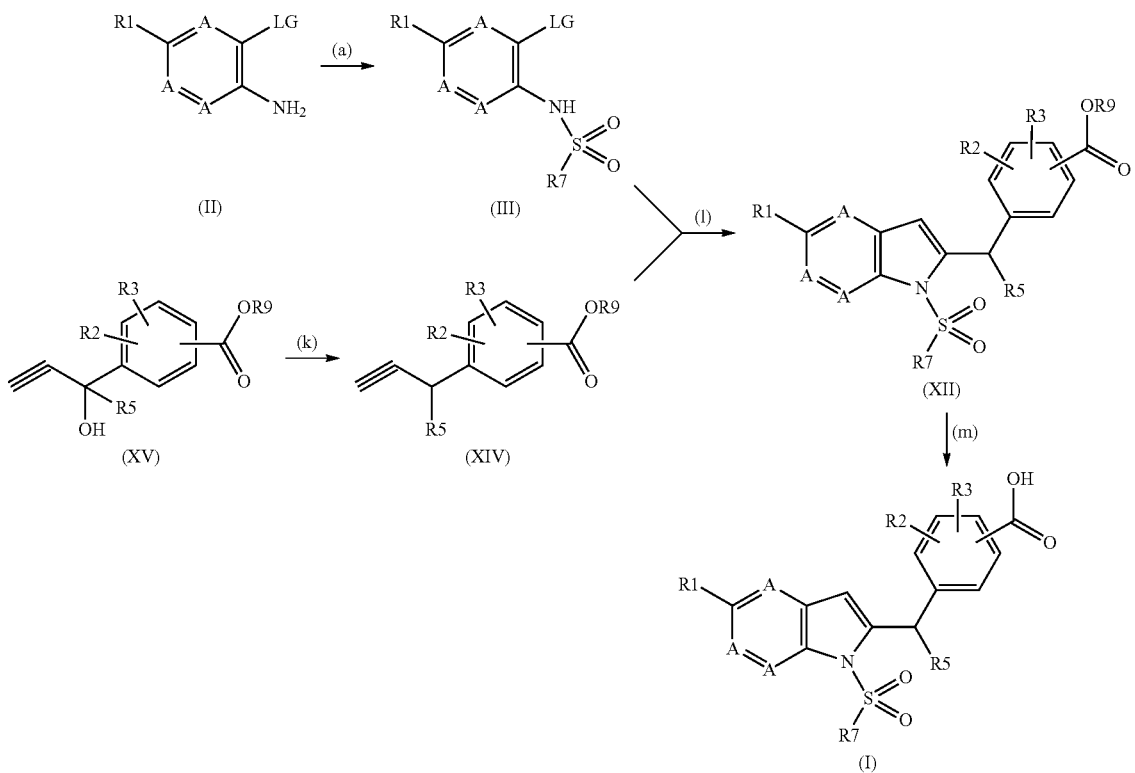

LG = I, Br, Tosylate

Step (a)

This step is identical to step (a) described for Scheme 1, and leads to the production of the compound of formula (III).

Step (k)

The acetylenic derivative of formula (XV) is reduced in the presence of a trialkylsilane, for instance triethylsilane, and an optional catalytic amount of an acid, for instance trifluoroacetic acid, in a suitable solvent, for instance DCM, at room temperature for a period of about 4 to 8 days. The compound of formula (XIV) is thus obtained.

Step (l)

The compounds of formulae (III) and (XIV) are reacted in the presence of copper iodide and of a palladium-based catalyst, for instance bis(triphenylphosphine)palladium(II) chloride, in a suitable solvent, for instance N,N-dimethylformamide (DMF). A suitable base, for instance diethylamine or triethylamine, is then added and the reaction mixture is heated for a period of about 1 to 6 hours at a temperature between room temperature and the reflux temperature of the solvent. According to one variant, the heating may be performed in a microwave oven for a period of about 5 to 30 minutes. The compound of formula (XII) is thus obtained.

Step (m)

When R9 is other than H, the ester function of the compound of formula (XII) is hydrolysed according to procedures that are well known to those skilled in the art, for example via the action of a mineral base such as lithium hydroxide, in a suitable solvent, for instance THF or a THF/water mixture, at a temperature between room temperature and the reflux temperature of the solvent. The compound of formula (I) is thus obtained.

According to a fifth embodiment, the compounds of formula (I) in which R8 represents H may be prepared as described in Scheme 5.

Step (a)

This step is identical to step (a) described for Scheme 1, and leads to the production of the compound of formula (III).

Step (n)

The compounds of formulae (III) and (XV) are reacted in the presence of copper iodide and a palladium-based catalyst, for instance bis(triphenylphosphine)palladium(II) chloride, in a suitable solvent, for instance DMF. A suitable base, for instance diethylamine or triethylamine, is then added, and the reaction mixture is heated for a period of about 1 to 6 hours at a temperature between room temperature and the reflux temperature of the solvent. According to one variant, the heating may be performed in a microwave oven for a period of about 5 to 30 minutes. The compound of formula (XIII) is thus obtained.

Step (o)

The compound of formula (XIII) is reduced in the presence of a trialkylsilane, for instance triethylsilane, boron trifluoride diethyl etherate and an optional catalytic amount of an acid, for instance trifluoroacetic acid, in a suitable solvent, for instance DCM, at room temperature for a period of about 6 to 18 hours. The compound of formula (XII) is thus obtained.

Step (m)

This step is identical to step (m) described for Scheme 4, and leads to the production of the compound of formula (I).

According to a sixth embodiment, the compounds of formula (I) in which R4 and R5 form, together with the carbon atom to which they are attached, an ethylene group ($C=CH_2$), R6 represents COOH and R8 represents H may be prepared as described in Scheme 6.

Scheme 5

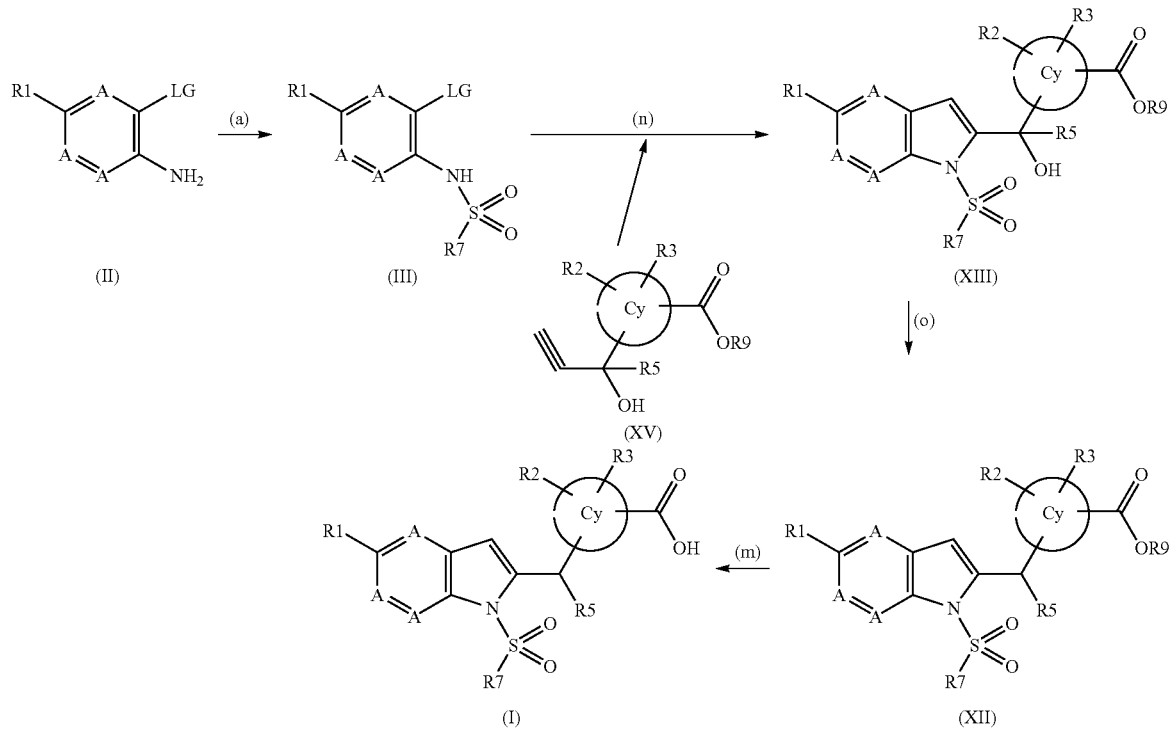

LG = I, Br, Tosylate

Scheme 6

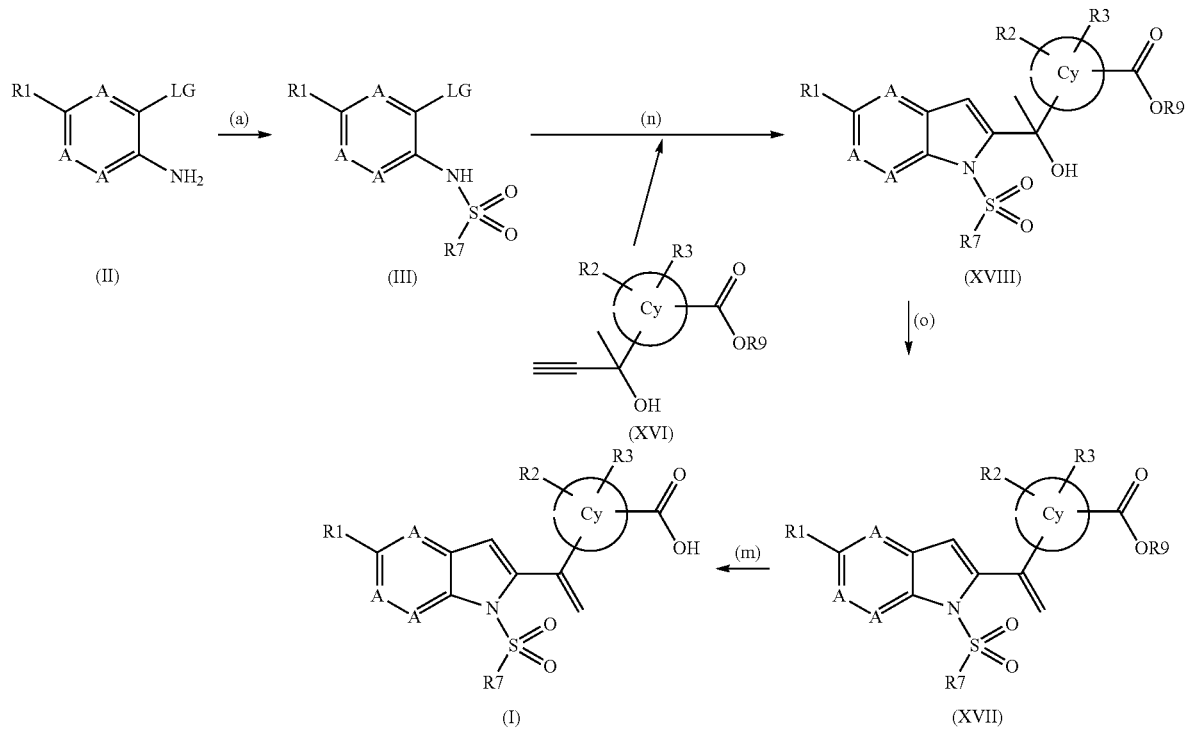

LG = I, Br, Tosylate

Step (a)

This step is identical to step (a) described for Scheme 1, and leads to the production of the compound of formula (III).

Step (n)

This step is identical to step (n) described for Scheme 5, and leads to the production of the compound of formula (XVIII).

Step (o)

This step is identical to step (o) described for Scheme 5, and leads to the production of the compound of formula (XVII).

Step (m)

This step is identical to step (m) described for Scheme 4, and leads to the production of the compound of formula (I).

According to a seventh embodiment, the compounds of formula (I) in which R4 and R5 form, together with the carbon atoms to which they are attached, a carbonyl group and R8 represents H may be prepared as described in Scheme 7.

Scheme 7

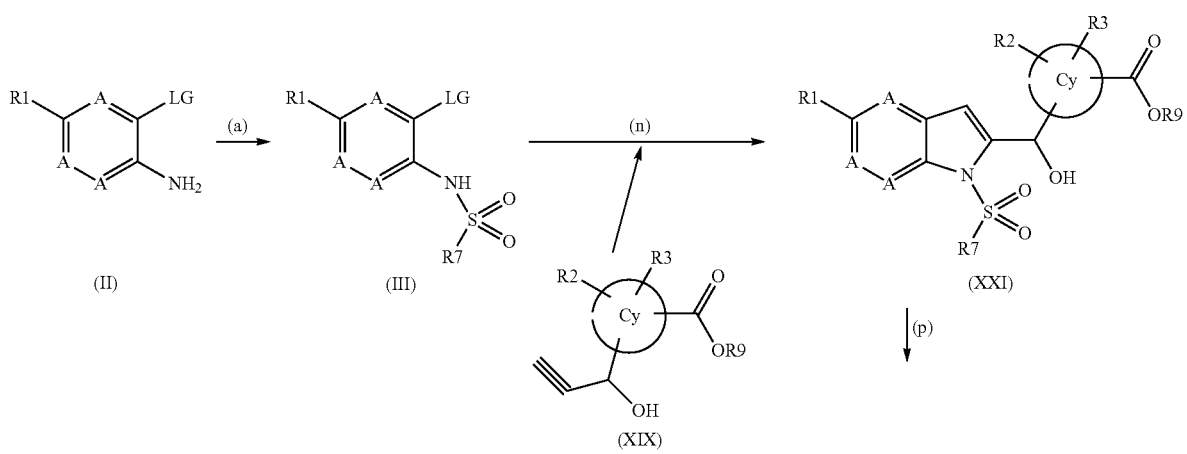

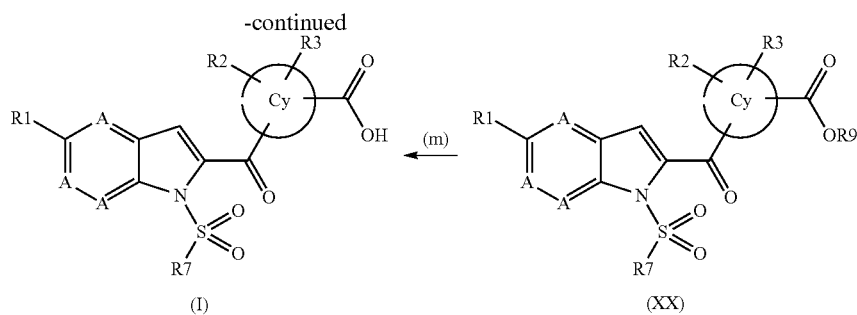

LG = I, Br, Tosylate

Step (a)
This step is identical to step (a) described for Scheme 1, and leads to the production of the compound of formula (III).
Step (n)
This step is identical to step (n) described for Scheme 5, and leads to the production of the compound of formula (XXI).
Step (p)
The compound of formula (XXI) is treated with a suitable oxidizing agent, for instance pyridinium dichromate, in a suitable solvent, for instance DCM, at room temperature for a period of about 6 to 18 hours. The compound of formula (XX) is thus obtained.
Step (m)
This step is identical to step (m) described for Scheme 4, and leads to the production of the compound of formula (I).

According to an eighth embodiment, the compounds of formula (I) in which R4 represents a halogen atom and R5 represents a hydrogen atom may be prepared as described in Scheme 8.

Step (a)
This step is identical to step (a) described for Scheme 1, and leads to the production of the compound of formula (III).
Step (n)
This step is identical to step (n) described for Scheme 5, and leads to the production of the compound of formula (XIII').
Step (q)
The compound of formula (XIII') is reacted with a halogenating agent, for instance 1-chloromethyl-4-fluoro-1,4-diazoniabicyclo[2.2.2]octane bis(tetrafluoroborate), at room temperature for about 30 minutes to 2 hours, to obtain the compound of formula I.

In general, the carboxylic acid function of the compounds of formula (I) in which R6 represents COOH may be advantageously replaced with a carboxylic acid bioisostere group according to methods that are well known to those skilled in the art, such as the methods described below.

The compounds of formula (I) according to the invention, in which R6 represents an acylhydrazine, acylhydrazine car- Scheme 8

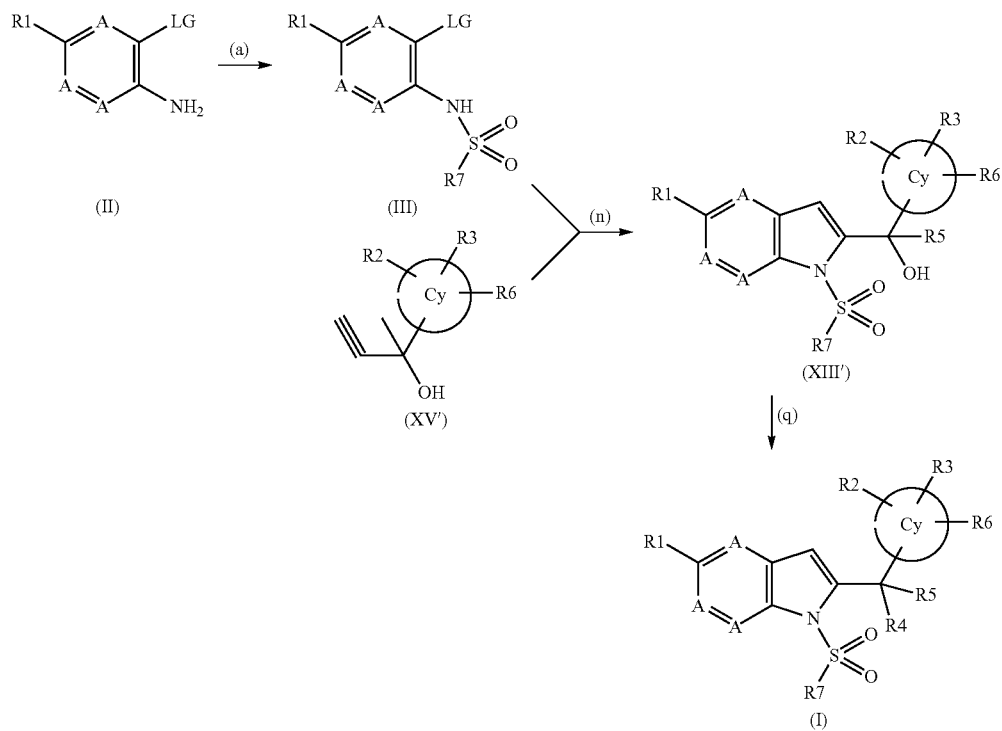

LG = I, Br, Tosylate boxylate or oxadiazolone bioisostere group, may be prepared according to a process that consists in:

a) reacting the compound of formula (I) in which R6 represents COOH with a carbazate in the presence of a coupling agent especially such as the 1-(3-dimethylaminopropyl)-3-ethylcarbodiimide (EDCI)/1-hydroxy-7-azabenzotriazole (HOAT) reagent pair, in an organic solvent in particular such as toluene, at room temperature for 2 to 24 hours, to give an acylhydrazine carboxylate compound of formula (I) in which R6 represents CONHNHCOOR11 and R11 represents a hydrogen atom or an alkyl group containing 1 to 4 carbon atoms;

b) if necessary, deprotecting the abovementioned compound of formula (I) according to a procedure that is well known to those skilled in the art, for instance by treating the said compound of formula (I) with an acid such as trifluoroacetic acid in a solvent in particular such as dichloromethane, to obtain an acylhydrazine;

c) if necessary, cyclizing the acylhydrazine in the presence of a coupling agent such as carbonyldiimidazole (CDI) in an organic solvent such as dichloromethane, at room temperature for 2 to 15 hours to obtain the oxadiazolone of formula (I) in which R6 represents:

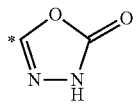

The compounds of formula (I) according to the invention, in which R6 represents a carboxamide bioisostere group, may be prepared according to a process that consists in reacting the compound of formula (I) in which R6 represents COOH with an amine in the presence of a coupling agent especially such as the 1-(3-dimethylaminopropyl)-3-ethyl-carbodiimide (EDCI)/1-hydroxy-7-azabenzotriazole (HOAT) reagent pair, in an organic solvent in particular such as dichloromethane, at room temperature for 2 to 24 hours to give a carboxamide compound of formula (I) in which R6 represents CONR12R13 and R12 and R13 independently represent a hydrogen atom or an alkyl group containing 1 to 4 carbon atoms.

The compounds of formula (I) according to the invention, in which R6 represents a sulfonylcarbamoyl bioisostere group or a derived group may be prepared according to a process that consists in coupling the compound of formula I in which R6 represents COOH with a sulfonamide in the presence of a coupling agent in particular such as the 1-(3-dimethylaminopropyl)-3-ethylcarbodiimide hydro chloride/4-dimethylaminopyridine (EDCI/DMAP) reagent pair in an organic solvent such as dichloromethane at room temperature for 12 to 24 hours.

The compounds of formula (I) according to the invention, in which R6 represents an isoxazole bioisostere group or a derived group such as an isoxazolone group, may be prepared according to the process that consists in:

a) activating the acid function of the compound of formula (I) in which R6 represents COOH using carbonyldiimidazole (CDI) and in reacting it with the magnesium salt of ethyl monomalonate;

b) cyclizing in the presence of hydroxylamine and in basic medium at room temperature for 2 to 4 days to obtain the compound of formula I in which R6 represents:

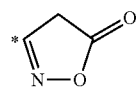

The compounds of formulae R7SO$_2$Cl, (HO)$_2$B-Cy(R2, R3)-R6, (II), (VI), (XV), (XV'), (XVI), (XIX) and (XXII) are commercially available or may be prepared according to procedures that are well known to those skilled in the art. The present invention relates to the preparation processes described above, and also to the intermediates used in these processes. In particular, a subject of the invention is the compounds of formulae (IV), (IV'), (V), (VII), (VIII), (IX), (X), (XII), (XIII), (XIII'), (XVII), (XVIII), (XX) and (XXI), and also the possible salts of these compounds.

The examples that follow, of the preparation of compounds according to formula (I), will allow the invention to be understood more clearly.

In these examples, which do not limit the scope of the invention, the term "preparation" denotes the examples describing the synthesis of intermediate compounds, and the term "examples" denotes the examples describing the synthesis of compounds of formula (I) according to the invention.

The following abbreviations have been used:

CuI copper iodide

DAST diethylaminosulfur trifluoride

DIBAL-H diisobutylaluminium hydride

DBU 1,8-diazabicyclo[5.4.0]undec-7-ene

DCM dichloromethane

DMF N,N-dimethylformamide

DMSO dimethyl sulfoxide eq. equivalent h hours

HCl hydrochloric acid min minutes mM millimoles

RT room temperature

TEMPO 2,2,6,6-tetramethylpiperidine-1-oxyl

TFA trifluoroacetic acid

THF tetrahydrofuran

The melting points (m.p.) were measured using an automatic machine (Optimelt) and the nuclear magnetic resonance spectral values were characterized by means of the chemical shift (δ) calculated relative to TMS (tetramethylsilane), by the number of protons associated with the signal and by the shape of the signal (s for singlet, d for doublet, t for triplet, q for quartet, m for multiplet, dd for doublet of doublets). The working frequency (in megahertz) and the solvent used are indicated for each compound.

Room temperature is 20° C.±5° C.

PREPARATION 1

3-(1,1-dimethylethyl)-N-(2-iodo-6-trifluoromethylpyridin-3-yl)benzenesulfonamide

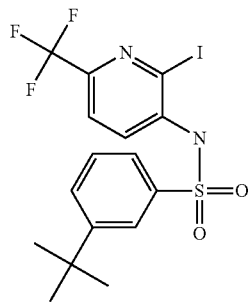 [SMILES: CC(C)(C)c1cccc(S(=O)(=O)Nc2ccc(C(F)(F)F)nc2I)c1]

9.07 g (38.96 mM) of 3-tert-butylbenzenesulfonyl chloride were added to a solution of 6.60 g (22.92 mM) of 2-iodo-6-trifluoromethylpyridin-3-ylamine in 10.0 mL of pyridine. This reaction mixture was stirred at room temperature overnight. The medium was diluted with water and then extracted with ethyl acetate. The organic phase was washed with 1N hydrochloric acid solution and then dried over magnesium sulfate, filtered and then concentrated under reduced pressure. 14.40 g of the evaporation residue were dissolved in 50.0 mL of 1,4-dioxane, 56.4 mL (169.28 mM) of 3M potassium hydroxide were added, and the reaction mixture was then refluxed for 1 hour. The medium was concentrated under reduced pressure. The residue was dissolved in water, and the solution was acidified with concentrated hydrochloric acid and then extracted twice with DCM. The organic phase was dried over magnesium sulfate, filtered and then concentrated under reduced pressure. The residue was washed with petroleum ether and then filtered on a Büchner funnel. The title product was obtained in the form of a white solid (8.80 g, yield=86%). m.p.=125° C.

PREPARATION 2

[1-(3-(1,1-dimethylethyl)phenylsulfonyl)-5-trifluoromethyl-1H-pyrrolo[3,2-b]pyridin-2-yl]methanol

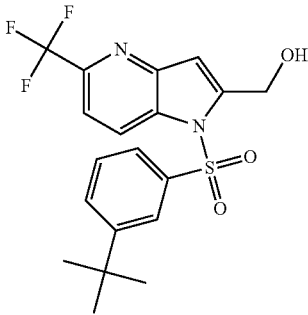 [SMILES: CC(C)(C)c1cccc(S(=O)(=O)n2c(CO)cc3nc(C(F)(F)F)ccc32)c1]

A solution of 2.00 g (4.13 mM) of 3-tert-butyl-N-(2-iodo-6-trifluoromethylpyridin-3-yl)benzenesulfonamide (Preparation 1) in 10.0 mL of DMF was prepared. 0.04 g (0.21 mM) of CuI, 0.14 g (6.19 mM) of bis(triphenylphosphine)palladium(II) chloride and 0.35 g (6.19 mM) of 2-propyn-1-ol were added. 5.0 mL of triethylamine were added to this mixture and this reaction mixture was then irradiated with microwaves for 10 minutes at 120° C. The medium was concentrated under reduced pressure, and the evaporation residue was purified by chromatography on silica gel using 90/10 and then 80/20 (v/v) cyclohexane/ethyl acetate as eluent. The title product was obtained in the form of a beige-coloured solid (1.29 g; yield=76%). m.p.=118° C.

PREPARATION 3

2-bromomethyl-1-(3-(1,1-dimethylethyl)phenylsulfonyl)-5-trifluoro-methyl-1H-pyrrolo[3,2-b]pyridine

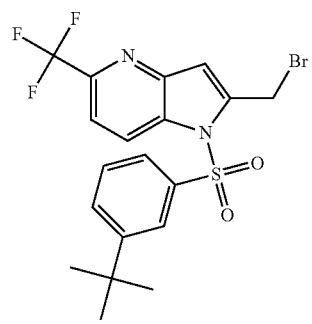 [SMILES: CC(C)(C)c1cccc(S(=O)(=O)n2c(CBr)cc3nc(C(F)(F)F)ccc32)c1]

A solution of 1.29 g (3.13 mM) of [1-(3-(1,1-dimethylethyl)phenylsulfonyl)-5-trifluoromethyl-1H-pyrrolo[3,2-b]pyridin-2-yl]methanol (Preparation 2) in 25.0 mL of DCM was prepared. 1.69 g (6.26 mM) of phosphorus tribromide were added dropwise. This reaction mixture was stirred for 4 days at room temperature. 100 mL of saturated potassium carbonate solution and 100 mL of water were added, and the mixture was then extracted twice with DCM (50 mL). The organic phases were combined, dried over magnesium sulfate, filtered and concentrated under reduced pressure. The title product was obtained in the form of a beige-coloured solid (1.62 g, yield=100%). m.p.=124° C.

EXAMPLE 1

5-[[1-[[3-(1,1-dimethylethyl)phenyl]sulfonyl]-5-(trifluoromethyl)-1H-pyrrolo[3,2-b]pyridin-2-yl]methyl]thiophene-2-carboxylic acid

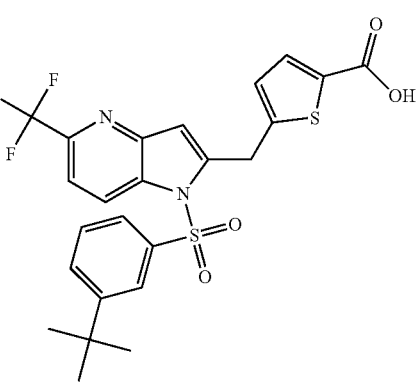

A solution of 230 mg (0.48 mM) of 2-bromomethyl-1-(3-tert-butylbenzene-sulfonyl)-5-trifluoromethyl-1H-pyrrolo[3,2-b]pyridine (Preparation 3) in 4.0 ml of ethanol and 1.0 mL of 1,4-dioxane was prepared. 99.8 mg (0.58 mM) of 5-(dihydroxyboryl)-2-thiophenecarboxylic acid, 39.5 mg (0.58 mM) of Pd(dppf)Cl$_2$.DCM complex and 80 mg (0.58 mM) of potassium carbonate were added to this solution. This reaction mixture was irradiated with microwaves for 20 minutes at 120° C. The medium was diluted with water and then extracted with ethyl acetate. The organic phase was washed with saturated saline solution and then dried over magnesium sulfate, filtered and concentrated under reduced pressure. The evaporation residue was purified by liquid chromatography with UV detection (LC-UV) (on a SunFire® C18 column) eluting with a water/methanol/0.1% TFA mixture. The fractions containing the expected product were combined and concentrated under reduced pressure. The title product was obtained in the form of an orange oil (25 mg, yield=10%).

$^1$H NMR (400 MHz, DMSO) δ=13.00 (s, 1H), 8.68 (d, 1H), 7.85 (d, 1H), 7.75 (d, 1H), 7.67-7.70 (m, 2H), 7.55 (d, 1H), 7.48 (t, 1H), 7.00 (d, 2H), 4.77 (s, 2H), 1.18 (s, 9H).

PREPARATION 4

4-methyl-5-nitro-2-trifluoromethylpyridine

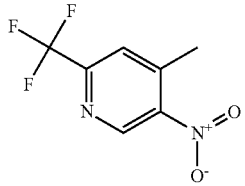

25.0 g (115.2 mM) of 2-bromo-4-methyl-5-nitropyridine, 44.3 g (230 mM) of methyl fluorosulfonyldifluoroacetate and 17.6 g (92.2 mM) of CuI were suspended in 250 mL of DMF. This reaction mixture was stirred at 120° C. for 48 hours. The medium was cooled and then diluted with 1000 mL of saturated ammonium chloride solution and 100 mL of ammonium hydroxide, and then stirred until homogenized. The product was extracted three times with ethyl acetate. The residue was purified by chromatography on silica gel, using 95/5 and then 90/10 (v/v) cyclohexane/ethyl acetate as eluent. The fractions containing the expected product were combined and concentrated under reduced pressure. The title product was obtained in the form of a brown oil (8.0 g, yield=34%).

$^1$H NMR (300 MHz, DMSO) δ=9.29 (s, 1H), 8.21 (s, 1H), 2.68 (s, 3H).

PREPARATION 5 ethyl 5-trifluoromethyl-1H-pyrrolo[2,3-c]pyridine-2-carboxylate

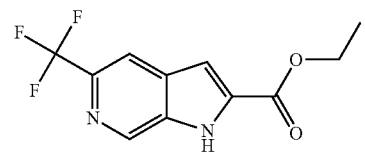 [SMILES: CCOC(=O)c1cc2cc(C(F)(F)F)ncc2[nH]1]

A solution of 6.0 g (23.29 mM) of 4-methyl-5-nitro-2-trifluoromethylpyridine (Preparation 4) in 14.8 mL (109.45 mM) diethyl oxalate was prepared. 8.65 g (56.8 mM) of DBU were added and the mixture was stirred for 4 hours at room temperature. The medium was concentrated under reduced pressure and the residue was then dissolved in 120 mL of acetic acid. This mixture was brought to 60° C. and 2.60 g (46.6 mM) of iron were added. The medium was heated at 70° C. overnight. The medium was diluted with water and the precipitate formed was filtered off and washed three times with water. The solid was dissolved in ethyl acetate, and the solution was filtered. The filtrate obtained was concentrated under reduced pressure. The title product was obtained in the form of a brown solid (5.70 g, yield=95%). m.p.=142° C.

PREPARATION 6 ethyl 1-(3-(1,1-dimethylethyl)phenylsulfonyl)-5-trifluoromethyl-1H-pyrrolo[2,3-c]pyridine-2-carboxylate

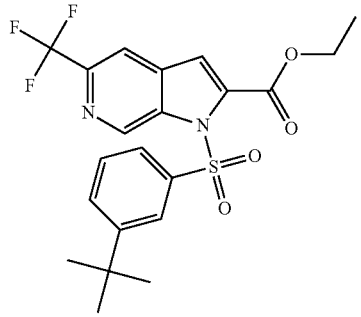 [SMILES: CCOC(=O)c1cc2cc(C(F)(F)F)ncc2n1S(=O)(=O)c1cccc(C(C)(C)C)c1]

1.55 g (38.7 mM) of sodium hydride at 60% in oil were suspended in 20.0 mL of THF under argon. A solution of 5.0 g (19.36 mM) of ethyl 5-trifluoromethyl-1H-pyrrolo[2,3-c]pyridine-2-carboxylate (Preparation 5) in 20.0 mL of THF was prepared and this solution was then added slowly to the reaction mixture. The medium was stirred for 1 hour at room temperature, followed by addition of 6.76 g (29.0 mM) of 3-tert-butylbenzenesulfonyl chloride, and this reaction mixture was stirred at room temperature overnight. The medium was diluted with water and then extracted with ethyl acetate. The organic phase was washed with saturated saline solution, dried over magnesium sulfate, filtered and concentrated under reduced pressure. The evaporation residue was purified by chromatography on silica gel using 90/10 (v/v) cyclohexane/ethyl acetate as eluent. The fractions containing the expected product were combined and concentrated under reduced pressure. The title product was obtained in the form of a white solid (7.25 g, yield=82%). m.p.=70° C.

PREPARATION 7

[1-(3-(1,1-dimethylethyl)phenylsulfonyl)-5-trifluoromethyl-1H-pyrrolo[2,3-c]pyridin-2-yl]methanol

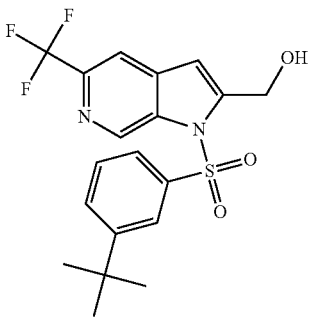 [SMILES: CC(C)(C)c1cccc(S(=O)(=O)n2c(CO)cc3cc(C(F)(F)F)ncc32)c1]

A solution of 7.25 g (15.9 mM) of ethyl 1-(3-(1,1-dimethylethyl)phenylsulfonyl)-5-trifluoromethyl-1H-pyrrolo[2,3-c]pyridine-2-carboxylate (Preparation 6) in 140 mL of toluene was prepared, under argon. This solution was cooled to −78° C. and 40 mL of DIBAL-H at 1.0 mol/L in toluene were added dropwise. This reaction mixture was stirred for 3 hours at −70° C. The medium was diluted with 300 mL of water, and sodium hydrogen carbonate solution and ethyl acetate were then added. This mixture was stirred for 2 days at room temperature. The organic phase was dried over magnesium sulfate, filtered and concentrated under reduced pressure. The evaporation residue was purified by chromatography on silica gel using a 90/10 to 70/30 (v/v) cyclohexane/ethyl acetate gradient. The fractions containing the expected product were combined and concentrated under reduced pressure. The title product was obtained in the form of a beige-coloured solid (4.08 g, yield=62%).

$^{1}$H NMR (300 MHz, DMSO) δ=9.43 (s, 1H), 8.19 (s, 1H), 8.00 (d, 1H), 7.93 (d, 1H), 7.80 (d, 1H), 7.57 (t, 1H), 6.99 (s, 1H), 5.85 (m, 1H), 4.92 (d, 2H), 1.23 (s, 9H)

PREPARATION 8

2-bromomethyl-1-(3-(1,1-dimethylethyl)phenylsulfonyl)-5-trifluoro-methyl-1H-pyrrolo[2,3-c]pyridine

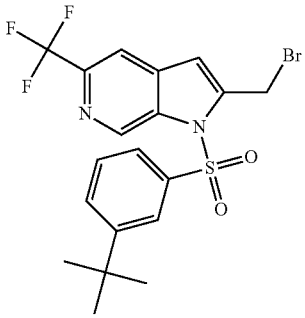 [SMILES: CC(C)(C)c1cccc(S(=O)(=O)n2c(CBr)cc3cc(C(F)(F)F)ncc32)c1]

This compound was obtained in the form of a white solid from the compound of Preparation 7, by following the procedure described in Preparation 3 (yield=68%). m.p.=115° C.

EXAMPLE 2

3-[[1-[[3-(1,1-dimethylethyl)phenyl]sulfonyl]-5-(trifluoromethyl)-1H-pyrrolo[2,3-c]pyridin-2-yl]methyl]-2-benzoic acid

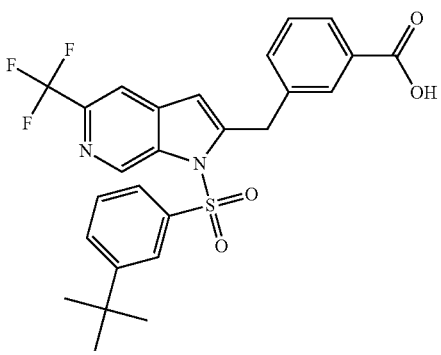 [SMILES: CC(C)(C)c1cccc(S(=O)(=O)n2c(Cc3cccc(C(=O)O)c3)cc3cc(C(F)(F)F)ncc32)c1]

This compound was obtained in the form of a white solid by following the procedure described in Example 1, from the compound of Preparation 8 and 3-(dihydroxyboryl)benzoic acid (yield=36%). m.p.=196° C.

EXAMPLE 3

2-chloro-4-[[1-[[3-(1,1-dimethylethyl)phenyl]sulfonyl]-5-(trifluoromethyl)-1H-pyrrolo[2,3-c]pyridin-2-yl]methyl]benzoic acid

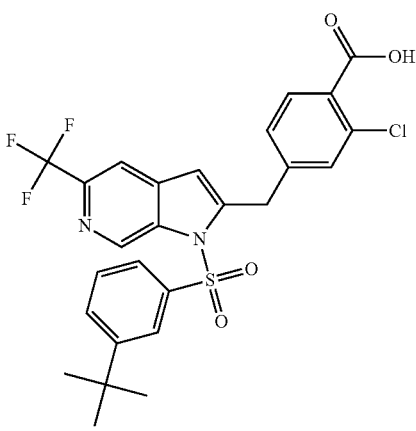 [SMILES: CC(C)(C)c1cccc(S(=O)(=O)n2c(Cc3ccc(C(=O)O)c(Cl)c3)cc3cc(C(F)(F)F)ncc32)c1]

This compound was obtained in the form of a white solid by following the procedure described in Example 1, from the compound of Preparation 8 and 4-(dihydroxyboryl)-2-chlorobenzoic acid (yield=21%).

¹H NMR (500 MHz, DMSO) δ=13.35 (s, 1H), 9.45 (s, 1H), 8.15 (s, 1H), 7.78 (m, 4H), 7.52 (t, 1H), 7.39 (s, 1H), 7.26 (d, 1H), 6.70 (s, 1H), 4.56 (s, 2H), 1.20 (s, 9H).

EXAMPLE 4

5-[[1-[[3-(1,1-dimethylethyl)phenyl]sulfonyl]-5-(trifluoromethyl)-1H-pyrrolo[2,3-c]pyridin-2-yl]methyl]furan-3-carboxylic acid

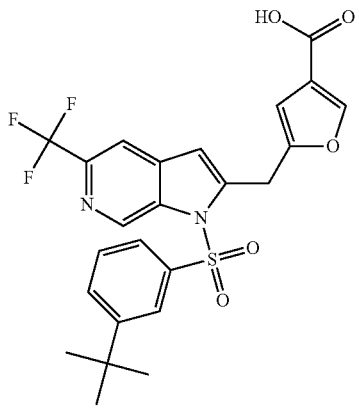 [SMILES: CC(C)(C)c1cccc(S(=O)(=O)n2c(Cc3cc(C(=O)O)co3)cc3cc(C(F)(F)F)ncc32)c1]

This compound was obtained in the form of a brown solid by following the procedure described in Example 1, from the compound of Preparation 8 and 5-(dihydroxyboryl)-3-furancarboxylic acid (yield=8%).

¹H NMR (500 MHz, DMSO) δ=12.70 (s, 1H), 9.45 (s, 1H), 8.22 (s, 1H), 8.14 (s, 1H), 7.82 (m, 3H), 7.54 (t, 1H), 6.72 (s, 1H), 6.49 (s, 1H), 4.59 (s, 2H), 1.20 (s, 9H).

EXAMPLE 5

5-[[1-[[3-(1,1-dimethylethyl)phenyl]sulfonyl]-5-(trifluoromethyl)-1H-pyrrolo[2,3-c]pyridin-2-yl]methyl]pyridine-3-carboxylic acid

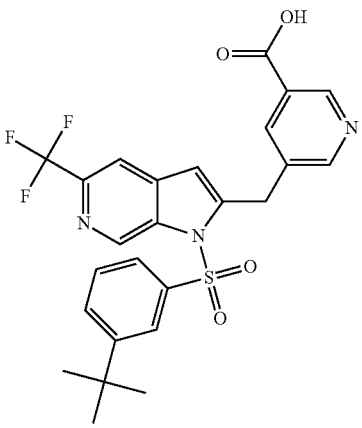 [SMILES: CC(C)(C)c1cccc(S(=O)(=O)n2c(Cc3cncc(C(=O)O)c3)cc3cc(C(F)(F)F)ncc32)c1]

This compound was obtained in the form of a brown-black solid by following the procedure described in Example 1, from the compound of Preparation 8 and 5-(dihydroxyboryl)-3-pyridinecarboxylic acid (yield=7%).

¹H NMR (500 MHz, DMSO) δ=13.50 (s, 1H), 9.45 (s, 1H), 8.96 (s, 1H), 8.73 (s, 1H), 8.14 (s, 1H), 8.07 (s, 1H), 7.77 (m, 3H), 7.51 (t, 1H), 6.72 (s, 1H), 4.63 (s, 2H), 1.19 (s, 9H).

EXAMPLE 6

4-[[1-[[3-(1,1-dimethylethyl)phenyl]sulfonyl]-5-(trifluoromethyl)-1H-pyrrolo[2,3-c]pyridin-2-yl]methyl]thiophene-2-carboxylic acid

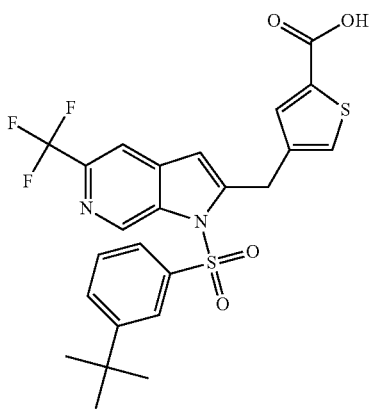 [SMILES: CC(C)(C)c1cccc(S(=O)(=O)n2c(Cc3csc(C(=O)O)c3)cc3cc(C(F)(F)F)ncc32)c1]

This compound was obtained in the form of a brown solid by following the procedure described in Example 1, from the compound of Preparation 8 and 4-(dihydroxyboryl)-2-thiophenecarboxylic acid (yield=11%).

¹H NMR (500 MHz, DMSO) δ=13.15 (s, 1H), 9.45 (s, 1H), 8.14 (s, 1H), 7.78 (m, 3H), 7.64 (s, 1H), 7.57 (s, 1H), 7.52 (t, 1H), 6.69 (s, 1H), 4.50 (s, 2H), 1.20 (s, 9H).

EXAMPLE 7

5-[[1-[[3-(1,1-dimethylethyl)phenyl]sulfonyl]-5-(trifluoromethyl)-1H-pyrrolo[2,3-c]pyridin-2-yl]methyl]-2-fluorobenzoic acid

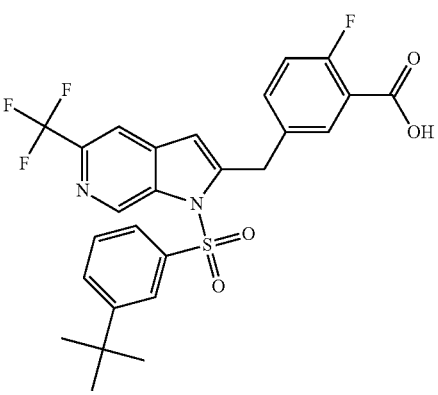 [SMILES: CC(C)(C)c1cccc(S(=O)(=O)n2c(Cc3ccc(F)c(C(=O)O)c3)cc3cc(C(F)(F)F)ncc32)c1]

This compound was obtained in the form of a brown solid by following the procedure described in Example 1, from the compound of Preparation 8 and 5-(dihydroxyboryl)-2-fluorobenzoic acid (yield=18%).

¹H NMR (500 MHz, DMSO) δ=13.25 (s, 1H), 9.40 (s, 1H), 8.13 (s, 1H), 7.77 (m, 3H), 7.69 (m, 1H), 7.51 (m, 2H), 7.27 (t, 1H), 6.62 (s, 1H), 4.53 (s, 2H), 1.20 (s, 9H).

PREPARATION 9

[1-(3-(1,1-dimethylethyl)phenylsulfonyl)-5-trifluoromethyl-1H-pyrrolo[3,2-b]pyridin-2-yl]acetonitrile

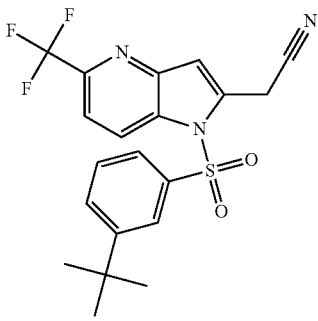 [SMILES: CC(C)(C)c1cccc(S(=O)(=O)n2c(CC#N)cc3nc(C(F)(F)F)ccc32)c1]

A solution of 1.62 g (3.41 mM) of 2-bromomethyl-1-(3-tert-butylbenzenesulfonyl)-5-trifluoromethyl-1H-pyrrolo[3,2-b]pyridine (Preparation 3) in 13 ml of DCM was prepared. 3.24 mL of water, 0.11 g (0.34 mM) of tetrabutylammonium bromide and 0.33 g (5.11 mM) of potassium cyanide were added. This reaction mixture was stirred at room temperature for three days. 100 mL of 10% sodium thiosulfate solution were added to the medium and the resulting mixture was extracted with 100 mL of DCM three times. The organic phases were dried over magnesium sulfate and combined, and then concentrated under reduced pressure. The evaporation residue was purified by chromatography on silica gel using 95/5 and then 90/10 (v/v) cyclohexane/ethyl acetate as eluent. The fractions containing the expected product were combined and concentrated under reduced pressure. The title product was obtained in the form of a yellow resin (280 mg, yield=19%).

$^1$H NMR (300 MHz, DMSO) δ=8.67 (d, 1H), 7.92-7.50 (m, 4H), 7.20 (s, 1H), 4.68 (s, 2H), 1.22 (s, 9H).

PREPARATION 10

2-[1-(3-(1,1-dimethylethyl)phenylsulfonyl)-5-trifluoromethyl-1H-pyrrolo[3,2-b]pyridin-2-yl]thioacetamide

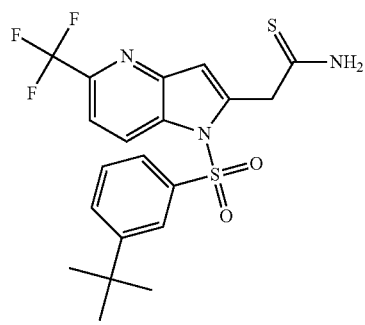 [SMILES: CC(C)(C)c1cccc(S(=O)(=O)n2c(CC(N)=S)cc3nc(C(F)(F)F)ccc32)c1]

A solution of 280 mg (0.66 mM) of [1-(3-(1,1-dimethylethyl)phenylsulfonyl)-5-trifluoromethyl-1H-pyrrolo[3,2-b]pyridin-2-yl]acetonitrile (Preparation 9) in 5.6 mL of THF and 11.2 mL of water was prepared. 494 mg (2.66 mM) of diethyl dithiophosphate were added, and this reaction mixture was then stirred overnight at 100° C. 2000 mg (10.74 mM) of diethyl dithiophosphate were added and stirring was continued at 100° C. for 4 hours. The medium was diluted with 100 mL of water and the mixture was then extracted 4 times with 50 mL of DCM. The organic phases were dried over magnesium sulfate, combined and concentrated under reduced pressure. The evaporation residue was purified by chromatography on silica gel using 90/10, then 80/20 and 70/30 cyclohexane/ethyl acetate as eluent. The fractions containing the expected product were combined and concentrated under reduced pressure. The title product was obtained in the form of a yellow solid (280.00 mg, yield=92%).

$^1$H NMR (300 MHz, DMSO) δ=8.62 (d, 1H), 7.76-7.83 (m, 4H), 7.57 (t, 1H), 6.95 (s, 1H), 4.40 (s, 2H), 1.22 (s, 9H).

EXAMPLE 8

2-[[1-[[3-(1,1-dimethylethyl)phenyl]sulfonyl]-5-(trifluoromethyl)-1H-pyrrolo[3,2-b]pyridin-2-yl]methyl]thiazole-4-carboxylic acid

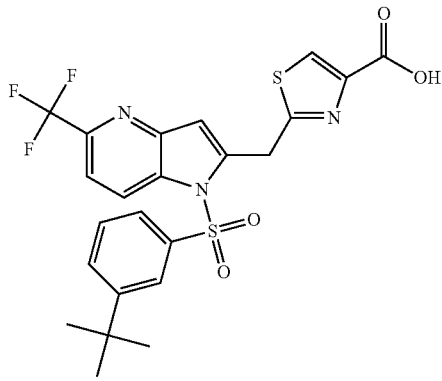 [SMILES: CC(C)(C)c1cccc(S(=O)(=O)n2c(Cc3nc(C(=O)O)cs3)cc3nc(C(F)(F)F)ccc32)c1]

A solution of 200 mg (0.44 mM) of 2-[1-(3-(1,1-dimethylethyl)phenylsulfonyl)-5-trifluoromethyl-1H-pyrrolo[3,2-b]pyridin-2-yl]thioacetamide (Preparation 10) in 2.0 mL of ethanol was prepared, and 110 mg (0.66 mM) of bromopyruvic acid were then added. This reaction mixture was stirred for 24 hours at room temperature. 150 mL of ethyl acetate were added to the medium, and the resulting mixture was then washed three times with 50 mL of 10% sodium carbonate and then with 50 mL of 0.2 M hydrochloric acid. The organic phase was dried over magnesium sulfate and then filtered and concentrated under reduced pressure. The title product was obtained in the form of a white solid (94 mg, yield=41%). m.p.=180° C.

PREPARATION 11

N-(3-iodo-5-trifluoromethylpyridin-2-yl)-4-(1-methylethyl)benzenesulfonamide

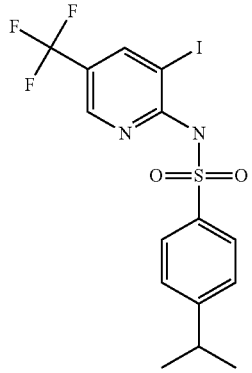 [SMILES: CC(C)c1ccc(S(=O)(=O)Nc2ncc(C(F)(F)F)cc2I)cc1]

This compound was obtained in the form of a yellow solid, by following the procedure described in Preparation 1, starting with 3-iodo-5-trifluoromethylpyridin-2-ylamine and 4-isopropylbenzenesulfonyl chloride (yield=52%). m.p.=124° C.

PREPARATION 12 methyl 4-prop-2-ynylbenzoate

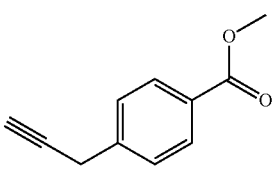

A solution of 5.97 g (31.4 mM) of methyl 4-(1-hydroxyprop-2-ynyl)benzoate in 40 mL of DCM was prepared. 20 mL (62.9 mM) of trifluoroacetic acid and then 10.0 mL (62.9 mM) of triethylsilane were added. This reaction mixture was stirred at room temperature for 7 days. The medium was concentrated under reduced pressure. The evaporation residue was purified by chromatography on silica gel using 95/5 (v/v) cyclohexane/ethyl acetate as eluent. The fractions containing the expected product were combined and concentrated under reduced pressure. The title product was obtained in the form of a white solid (3.23 g, yield=61%). m.p.=78° C.

EXAMPLE 9 methyl 4-[1-(4-(1-methylethyl)phenylsulfonyl)-5-trifluoromethyl-1H-pyrrolo[2,3-b]pyridin-2-ylmethyl]benzoate

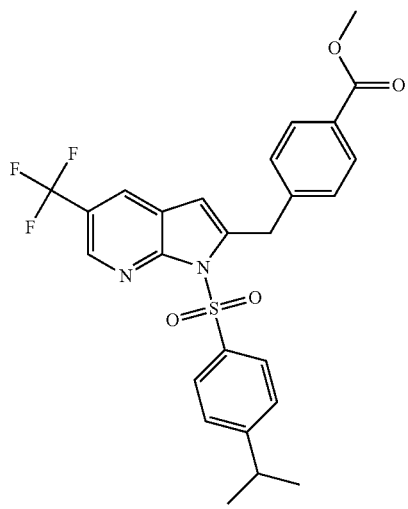 [SMILES: COC(=O)c1ccc(Cc2cc3cc(C(F)(F)F)cnc3n2S(=O)(=O)c2ccc(C(C)C)cc2)cc1]

This compound was obtained in the form of a beige-coloured solid by following the procedure described in Preparation 2, starting with the compounds of Preparations 11 and 12 (yield=56%). m.p.=123° C.

EXAMPLE 10

4-[[1-[[3-(1-methylethyl)phenyl]sulfonyl]-5-(trifluoromethyl)-1H-pyrrolo[2,3-b]pyridin-2-yl]methyl]benzoic acid

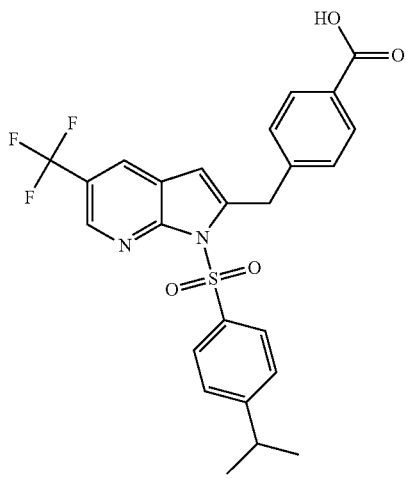 [SMILES: CC(C)c1ccc(S(=O)(=O)n2c(Cc3ccc(C(=O)O)cc3)cc3cc(C(F)(F)F)cnc32)cc1]

A solution of 140 mg (0.27 mM) of methyl 4-[1-(4-(1-methylethyl)phenylsulfonyl)-5-trifluoromethyl-1H-pyrrolo[2,3-b]pyridin-2-ylmethyl]-benzoate (Example 9) in 16.0 mL of THF and 4.0 mL of water was prepared. 13.65 mg (0.33 mM) of lithium hydroxide were added, and this reaction mixture was stirred at room temperature for 22 hours. The medium was diluted with water and then acidified with concentrated hydrochloric acid and extracted twice with DCM. The organic phase was dried over magnesium sulfate, filtered and then concentrated under reduced pressure. The evaporation residue was purified by liquid chromatography with UV detection (LC-UV) (on a SunFire® C18 column) with a water/acetonitrile/0.1% TFA mixture as eluent. The fractions containing the expected product were combined and concentrated under reduced pressure. The title product was obtained in the form of a white solid (113 mg, yield=83%). m.p.=218° C.

PREPARATION 13

4-iodo-6-trifluoromethylpyridin-3-ylamine

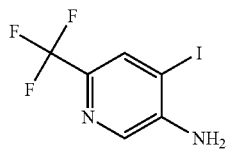

a) tert-butyl (6-trifluoromethylpyridin-3-yl)carbamate

A solution of 5.0 g (30.84 mM) of 3-amino-6-(trifluoromethyl)pyridine and 6.73 g (30.84 mM) of di-tert-butyl dicarbonate in 30 mL of 1,4-dioxane was prepared. This reaction mixture was stirred at reflux for 19 hours. 8.08 g (37.01 mM) of di-tert-butyl dicarbonate were added and the medium was stirred at reflux for 24 hours. 6.73 g (30.84 mM) of di-tert-butyl dicarbonate were added and the medium was stirred at reflux for 24 hours. The medium was concentrated under reduced pressure and the evaporation residue was purified by chromatography on silica gel using 90/10 (v/v) cyclohexane/ethyl acetate as eluent. The fractions containing the expected product were combined and concentrated under reduced pressure. The protected product was obtained in the form of a beige-coloured solid (10.9 g, yield=100%). m.p.=117° C.

b) tert-butyl (4-iodo-6-trifluoromethylpyridin-3-yl)carbamate

A solution of 10.80 g (41.19 mM) of tert-butyl (6-trifluoromethylpyridin-3-yl)carbamate in 300 mL of diethyl ether was prepared. 15.5 mL of N,N,N',N'tetramethylethylenediamine were added. This reaction mixture was cooled to −78° C. in a bath of cardice-acetone, followed by dropwise addition over 5 minutes of 64.3 mL (103 mM) of 1.60 M n-butyllithium in hexane. The medium was stirred for 30 minutes at −10° C. and then cooled to −78° C. A solution of 13.59 g (53.5 mM) of iodine in 16.0 mL of THF was added rapidly. The reaction mixture was allowed to warm to room temperature, and was stirred at room temperature for 16 hours. The medium was hydrolysed with 200 mL of water and then with 400 mL of saturated sodium bisulfite solution. It was then extracted with ether. The organic phase was dried over magnesium sulfate, filtered and concentrated under reduced pressure. The evaporation residue was purified by chromatography on silica gel using 100/0 and then 95/5 (v/v) cyclohexane/ethyl acetate as eluent. The fractions containing the expected product were combined and concentrated under reduced pressure. The iodo product was obtained in the form of a yellow oil (5.04 g, yield=37%).

$^1$H NMR (250 MHz, DMSO) δ=9.05 (broad s, 1H), 8.62 (s, 1H), 8.36 (s, 1H), 1.40 (s, 9H).

c) 4-iodo-6-trifluoromethylpyridin-3-ylamine

A solution of 5.04 g (13 mM) of tert-butyl (4-iodo-6-trifluoromethylpyridin-3-yl)carbamate in 100 mL of DCM was prepared. 10 mL of trifluoroacetic acid were added to this solution. This reaction mixture was stirred at room temperature for 18 hours. The medium was diluted with water and then extracted with DCM. The organic phase was dried over magnesium sulfate, filtered and concentrated under reduced pressure. The evaporation residue was purified by chromatography on silica gel using 100/0 then 95/5 and 90/10 (v/v) cyclohexane/ethyl acetate as eluent. The fractions containing the expected product were combined and concentrated under reduced pressure. The title product was obtained in the form of a beige-coloured solid (620.00 mg, yield=16%). m.p.=116° C.

PREPARATION 14

N-(2-iodo-4-trifluoromethylpyridin-3-yl)(3,4-dihydro-4-methyl-2H-1,4-benzoxazin-6-yl)sulfonamide

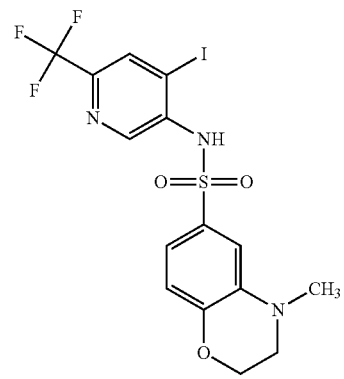 [SMILES: CN1CCOc2ccc(S(=O)(=O)Nc3cnc(C(F)(F)F)cc3I)cc21]

This compound was obtained in the form of a yellow oil by following the procedure described in Preparation 1, starting with 4-iodo-6-trifluoromethylpyridin-3-ylamine (Preparation 13) and 3,4-dihydro-4-methyl-2H-1,4-benzoxazin-6-ylsulfonyl chloride (yield=68%).

$^1$H NMR (300 MHz, DMSO) δ=10.14 (s, 1H), 8.35 (s, 1H), 8.26 (s, 1H), 6.95 (m, 2H), 6.80 (d, 1H), 4.29 (t, 2H), 3.29 (t, 2H), 2.80 (s, 3H).

EXAMPLE 11 methyl 4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]benzoate

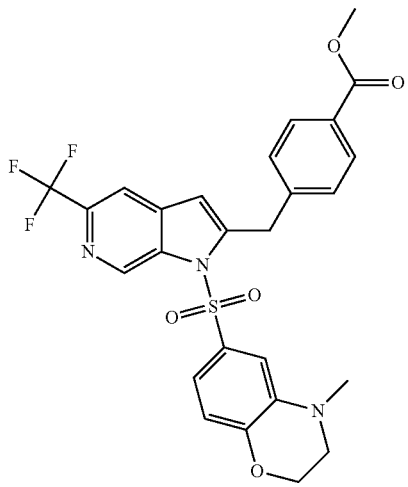 [SMILES: COC(=O)c1ccc(Cc2cc3cc(C(F)(F)F)ncc3n2S(=O)(=O)c2ccc3c(c2)N(C)CCO3)cc1]

EXAMPLE 12

4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]benzoic acid

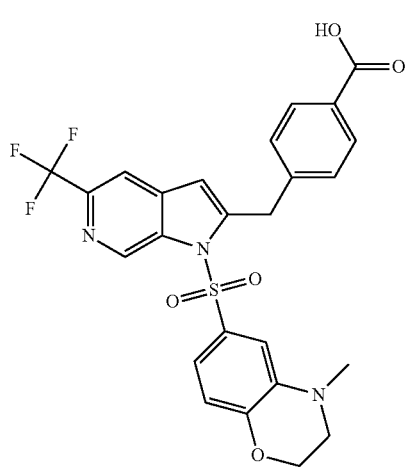 [SMILES: CN1CCOc2ccc(S(=O)(=O)n3c(Cc4ccc(C(=O)O)cc4)cc4cc(C(F)(F)F)ncc43)cc21]

This compound was obtained in the form of a white solid by following the procedure described in Example 10, starting with the compound of Example 11 (yield=43%). m.p.=192° C.

PREPARATION 15

N-(4-trifluoromethyl-6-iodopyridin-3-yl)-4-(1-methylethyl)benzenesulfonamide

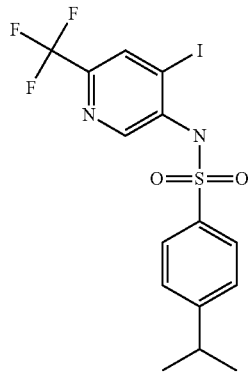 [SMILES: CC(C)c1ccc(S(=O)(=O)Nc2cnc(C(F)(F)F)cc2I)cc1]

This compound was obtained in the form of a beige-coloured solid, by following the procedure described in Preparation 1, starting with 4-iodo-6-trifluoromethylpyridin-3-ylamine (Preparation 13) and 4-(1-methylethyl)benzenesulfonyl chloride (yield=95%). m.p.=156° C.

EXAMPLE 13 methyl 4-[1-(4-(1-methylethyl)phenylsulfonyl)-5-trifluoromethyl-1H-pyrrolo[2,3-c]pyridin-2-ylmethyl]benzoate

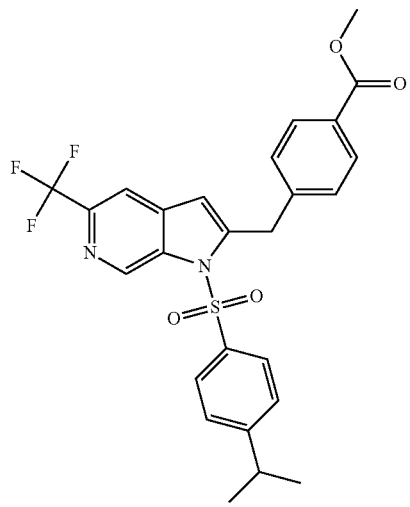 [SMILES: COC(=O)c1ccc(Cc2cc3cc(C(F)(F)F)ncc3n2S(=O)(=O)c2ccc(C(C)C)cc2)cc1]

This compound was obtained in the form of a beige-coloured solid by following the procedure described in Preparation 2, starting with the compounds of Preparations 12 and 15 (yield=33%). m.p.=160° C.

EXAMPLE 14

4-[[1-[[4-(1-methylethyl)phenyl]sulfonyl]-5-(trifluoromethyl)-1H-pyrrolo[2,3-c]pyridin-2-yl]methyl]benzoic acid

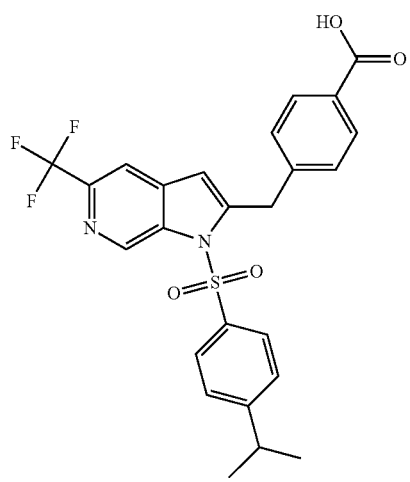 [SMILES: CC(C)c1ccc(S(=O)(=O)n2c(Cc3ccc(C(=O)O)cc3)cc3cc(C(F)(F)F)ncc32)cc1]

This compound was obtained in the form of a white solid by following the procedure described in Example 10, starting with the compound of Example 13 (yield=24%). m.p.=218° C.

PREPARATION 16

N-(2-iodo-6-trifluoromethylpyridin-3-yl)-4-(1-methylethyl)benzenesulfonamide

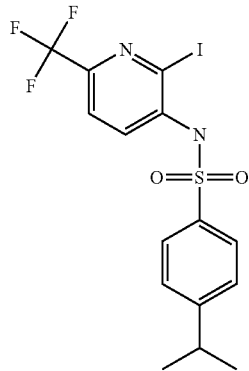 [SMILES: CC(C)c1ccc(S(=O)(=O)Nc2ccc(C(F)(F)F)nc2I)cc1]

This compound was obtained in the form of a pale yellow solid, by following the procedure described in Preparation 1, starting with 2-iodo-6-trifluoromethylpyridin-3-ylamine and 4-isopropylbenzenesulfonyl chloride (yield=98%).

$^1$H NMR (300 MHz, DMSO) δ=10.35 (s, 1H), 7.87 (d, 1H), 7.72 (dd, 2H), 7.62 (d, 1H), 7.48 (d, 2H), 2.98 (m, 1H), 1.20 (d, 6H).

EXAMPLE 15 methyl 4-[1-(4-(1-methylethyl)phenylsulfonyl)-5-trifluoromethyl-1H-pyrrolo[3,2-b]pyridin-2-ylmethyl]benzoate

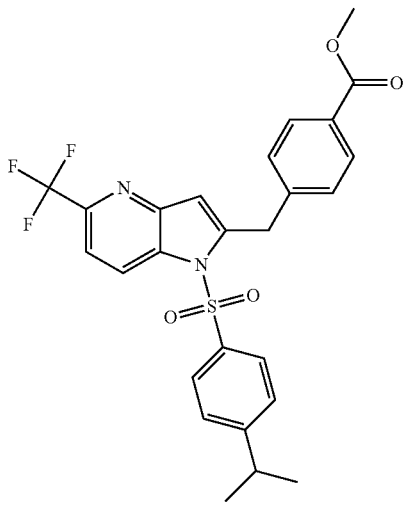

This compound was obtained in the form of a beige-coloured solid by following the procedure described in Preparation 2, starting with the compounds of Preparations 12 and 16 (yield=15%). m.p.=98.5° C.

EXAMPLE 16

4-[1-(4-(1-methylethyl)phenylsulfonyl)-5-trifluoromethyl-1H-pyrrolo[3,2-b]pyridin-2-ylmethyl]benzoic acid

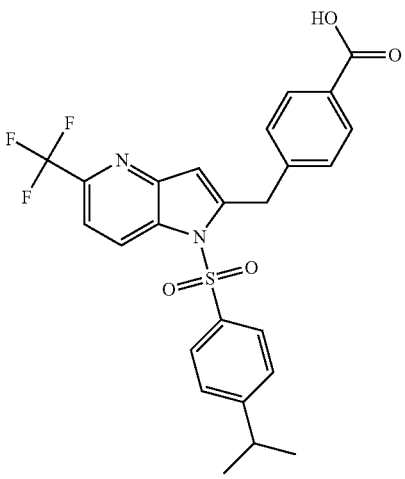 [SMILES: CC(C)c1ccc(S(=O)(=O)n2c(Cc3ccc(C(=O)O)cc3)cc3nc(C(F)(F)F)ccc32)cc1]

This compound was obtained in the form of a white solid by following the procedure described in Example 10, starting with the compound of Example 15 (yield=14%).

$^1$H NMR (500 MHz, DMSO) δ=12.89 (s, 1H), 8.66 (d, 1H), 7.83 (d, 3H), 7.72 (d, 2H), 7.36 (d, 2H), 7.30 (d, 2H), 6.84 (s, 1H), 4.58 (s, 2H), 2.91 (m, 1H), 1.13 (d, 6H).

PREPARATION 17

N-(3-iodo-5-trifluoromethylpyridin-2-yl)(3,4-dihydro-4-methyl-2H-1,4-benzoxazin-6-yl)sulfonamide

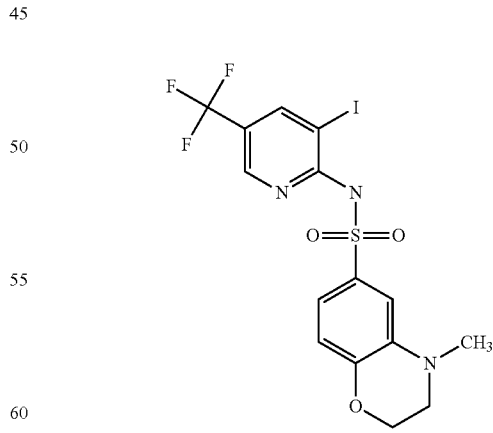

This compound was obtained in the form of a brown oil by following the procedure described in Preparation 1, starting with 3-iodo-5-trifluoromethylpyridin-2-ylamine and 3,4-dihydro-4-methyl-2H-1,4-benzoxazin-6-ylsulfonyl chloride (yield=66%).

$^1$H NMR (300 MHz, DMSO) δ=10.43 (s, 1H), 8.54 (s, 2H), 7.33 (s, 1H), 7.24 (d, 1H), 6.80 (d, 1H), 4.28 (t, 2H), 3.28 (t, 2H), 2.88 (s, 3H).

EXAMPLE 17 methyl 4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]benzoate

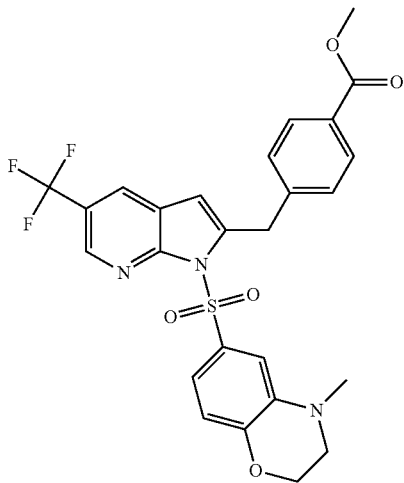 [SMILES: COC(=O)c1ccc(Cc2cc3cc(C(F)(F)F)cnc3n2S(=O)(=O)c2ccc3c(c2)N(C)CCO3)cc1]

This compound was obtained in the form of an orange solid by following the procedure described in Preparation 2, starting with the compounds of Preparations 12 and 17 (yield=30%). m.p.=202° C.

EXAMPLE 18

4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]benzoic acid

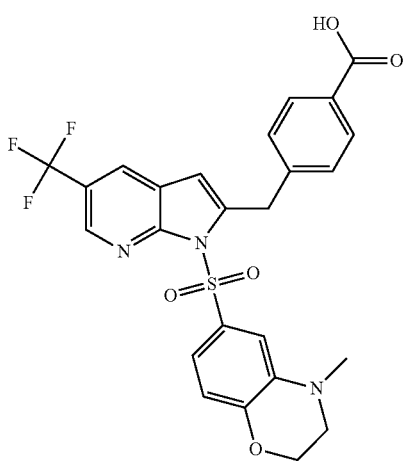 [SMILES: CN1CCOc2ccc(S(=O)(=O)n3c(Cc4ccc(C(=O)O)cc4)cc4cc(C(F)(F)F)cnc43)cc21]

This compound was obtained in the form of a white solid by following the procedure described in Example 10, starting with the compound of Example 17 (yield=21%). m.p.=234° C.

PREPARATION 18

N-(6-chloro-4-iodopyridin-3-yl)-4-(1-methylethyl)benzenesulfonamide

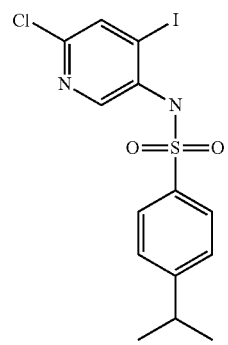 [SMILES: CC(C)c1ccc(S(=O)(=O)Nc2cnc(Cl)cc2I)cc1]

This compound was obtained in the form of an orange solid, by following the procedure described in Preparation 1, starting with 6-chloro-4-iodopyridin-3-ylamine and 4-isopropylbenzenesulfonyl chloride (yield=97%). m.p.=160° C.

EXAMPLE 19 methyl 4-[1-(4-(1-methylethyl)phenylsulfonyl)-5-chloro-1H-pyrrolo[2,3-c]pyridin-2-ylmethyl]benzoate

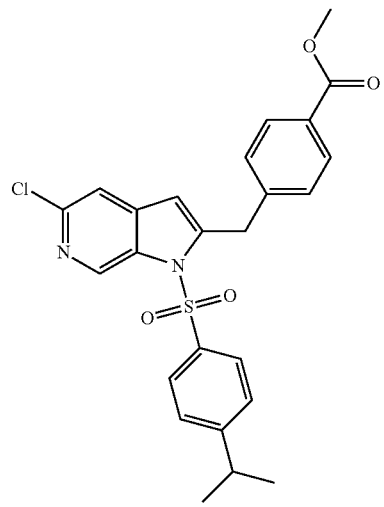 [SMILES: COC(=O)c1ccc(Cc2cc3cc(Cl)ncc3n2S(=O)(=O)c2ccc(C(C)C)cc2)cc1]

This compound was obtained in the form of a brown solid by following the procedure described in Preparation 2, starting with the compounds of Preparations 12 and 18 (yield=44%). m.p.=123° C.

EXAMPLE 20

4-[[5-chloro-1-[[4-(1-methylethyl)phenyl]sulfonyl]-1H-pyrrolo[2,3-c]pyridin-2-yl]methyl]benzoic acid

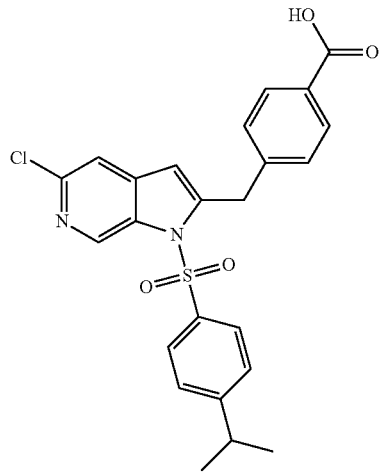 [SMILES: CC(C)c1ccc(S(=O)(=O)n2c(Cc3ccc(C(=O)O)cc3)cc3cc(Cl)ncc32)cc1]

This compound was obtained in the form of a beige-coloured solid by following the procedure described in Example 10, starting with the compound of Example 19 (yield=13%). m.p.=228° C.

EXAMPLE 21 methyl 4-[1-(3-(1,1-dimethylethyl)phenylsulfonyl)-5-trifluoromethyl-1H-pyrrolo[3,2-b]pyridin-2-ylmethyl]benzoate

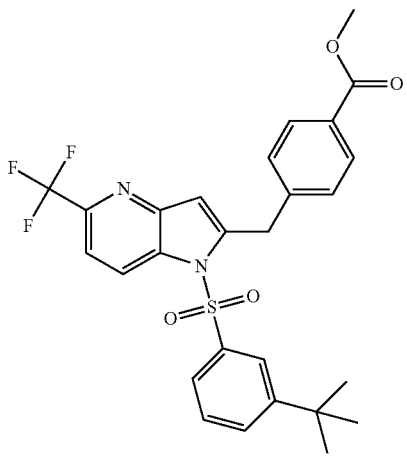 [SMILES: COC(=O)c1ccc(Cc2cc3nc(C(F)(F)F)ccc3n2S(=O)(=O)c2cccc(C(C)(C)C)c2)cc1]

This compound was obtained in the form of an orange paste by following the procedure described in Preparation 2, starting with the compounds of Preparations 1 and 12 (yield=4%).

$^1$H NMR (300 MHz, DMSO) δ=8.67 (d, 1H), 7.86 (m, 3H), 7.73 (d, 1H), 7.71 (d, 1H), 7.62 (d, 1H), 7.46 (t, 1H), 7.36 (d, 2H), 6.85 (s, 1H), 4.60 (s, 2H), 3.45 (s, 3H), 1.18 (s, 9H).

EXAMPLE 22

4-[[1-[[3-(1,1-dimethylethyl)phenyl]sulfonyl]-5-(trifluoromethyl)-1H-pyrrolo[3,2-b]pyridin-2-yl]methyl]benzoic acid

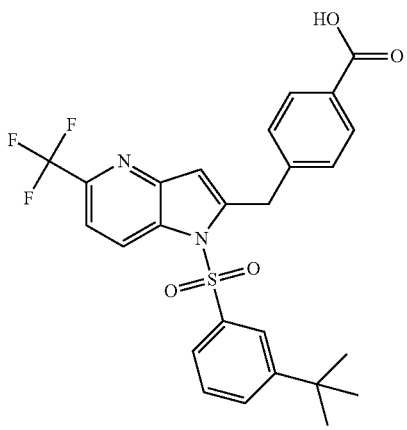 [SMILES: CC(C)(C)c1cccc(S(=O)(=O)n2c(Cc3ccc(C(=O)O)cc3)cc3nc(C(F)(F)F)ccc32)c1]

This compound was obtained in the form of a white solid by following the procedure described in Example 10, starting with the compound of Example 21 (yield=33%). m.p.=240° C.

PREPARATION 19

N-(3-iodo-5-trifluoromethylpyridin-2-yl)-3-(1-methylethyl)benzenesulfonamide

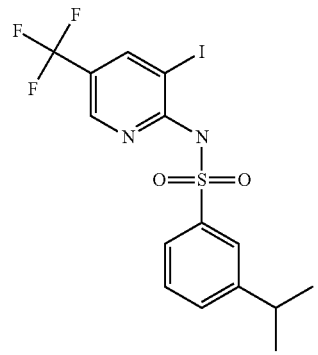 [SMILES: CC(C)c1cccc(S(=O)(=O)Nc2ncc(C(F)(F)F)cc2I)c1]

This compound was obtained in the form of a yellow oil by following the procedure described in Preparation 1, starting with 3-iodo-5-trifluoromethylpyridin-2-ylamine and 3-isopropylbenzenesulfonyl chloride (yield=84%).

$^1$H NMR (300 MHz, DMSO) δ=10.70 (s, 1H), 8.55 (s, 1H), 8.44 (s, 1H), 7.91 (s, 1H), 7.62 (d, 1H), 7.51 (m, 2H), 3.00 (m, 1H), 1.23 (d, 6H).

EXAMPLE 23 methyl 4-{hydroxy[1-(3-(1-methylethyl)phenylsulfonyl)-5-trifluoro-methyl-1H-pyrrolo[2,3-b]pyridin-2-yl]methyl}benzoate

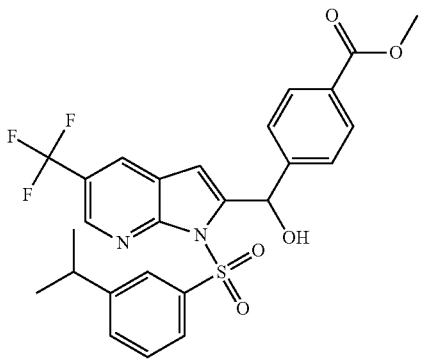 [SMILES: COC(=O)c1ccc(C(O)c2cc3cc(C(F)(F)F)cnc3n2S(=O)(=O)c2cccc(C(C)C)c2)cc1]

This compound was obtained in the form of a yellow oil by following the procedure described in Preparation 2, from the compound of Preparation 19 and methyl 4-(1-Hydroxyprop-2-ynyl)benzoate (yield=60%).

$^1$H NMR (300 MHz, DMSO) δ=8.72 (s, 1H), 8.49 (s, 1H), 7.98 (d, 2H), 7.79 (d, 1H), 7.54 (m, 4H), 7.43 (t, 1H), 6.86 (s, 1H), 6.57 (m, 2H), 3.87 (s, 3H), 2.74 (m, 1H), 1.08 (dd, 6H).

EXAMPLE 24 methyl 4-[1-(3-(1-methylethyl)phenylsulfonyl)-5-trifluoromethyl-1H-pyrrolo[2,3-b]pyridin-2-ylmethyl]benzoate

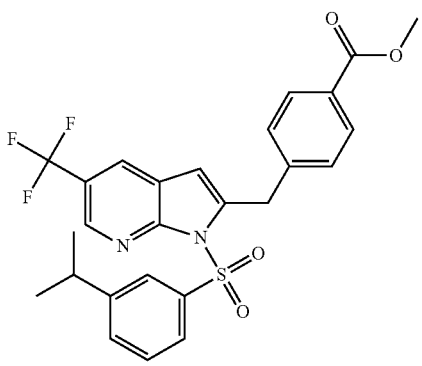 [SMILES: COC(=O)c1ccc(Cc2cc3cc(C(F)(F)F)cnc3n2S(=O)(=O)c2cccc(C(C)C)c2)cc1]

A solution of 220 mg (0.41 mM) of methyl 4-{hydroxy[1-(3-isopropylbenzenesulfonyl)-5-trifluoromethyl-1H-pyrrolo[2,3-b]pyridin-2-yl]methyl}-benzoate (Example 23) in 10 mL of DCM was prepared. This solution was cooled to 0° C. with an ice bath, and 4.19 mL (33.05 mM) of boron trifluoride diethyl etherate (4.19 mL; 33.05 mM; 80.00 eq.) and 2.0 mL (12.39 mM) of triethylsilane were then added. This reaction mixture was stirred at room temperature overnight. The medium was hydrolysed slowly with saturated sodium carbonate solution and then extracted with DCM. The organic phase was washed with water and then dried over magnesium sulfate, filtered and concentrated under reduced pressure. The evaporation residue was purified by chromatography on silica gel using 95/5 and then 90/10 (v/v) cyclohexane/ethyl acetate as eluent. The fractions containing the expected product were combined and concentrated under reduced pressure. The product obtained was washed with cyclohexane and then filtered through Whatman filter paper. The title product was obtained in the form of a white solid (90 mg, yield=42%). m.p.=110° C.

EXAMPLE 25

4-[[1-[[3-(1-methylethyl)phenyl]sulfonyl]-5-(trifluoromethyl)-1H-pyrrolo[2,3-b]pyridin-2-yl]methyl]benzoic acid

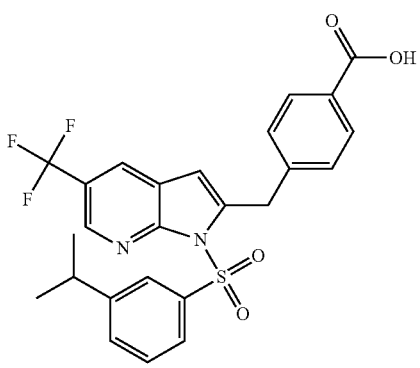

This compound was obtained in the form of a white solid by following the procedure described in Example 10, starting with the compound of Example 24 (yield=17%). m.p.=203° C.

PREPARATION 20

N-(3-iodo-5-trifluoromethylpyridin-2-yl)-3-(1,1-dimethylethyl)-benzenesulfonamide

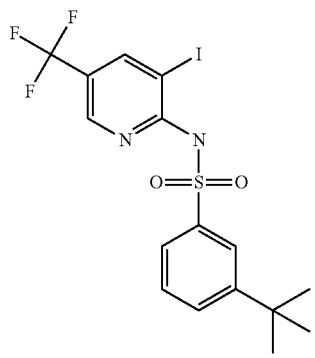 [SMILES: CC(C)(C)c1cccc(S(=O)(=O)Nc2ncc(C(F)(F)F)cc2I)c1]

This compound was obtained in the form of a beige-coloured solid by following the procedure described in Preparation 1, starting with 3-iodo-5-trifluoromethylpyridin-2-ylamine and 3-tert-butylbenzensulfonyl chloride (yield=72%). m.p.=135° C.

EXAMPLE 26 methyl 4-{hydroxy[1-(3-(1,1-dimethylethyl)phenyl-sulfonyl)-5-trifluoromethyl-1H-pyrrolo[2,3-b]pyridin-2-yl]methyl}benzoate

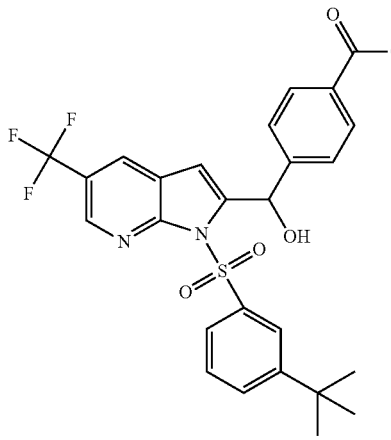

This compound was obtained in the form of a yellow oil by following the procedure described in Preparation 2, from the compound of Preparation 20 and methyl 4-(1-hydroxyprop-2-ynyl)benzoate (yield=92%).

$^1$H NMR (300 MHz, DMSO) δ=8.73 (d, 1H), 8.47 (d, 1H), 8.12 (d, 1H), 7.97 (d, 2H), 7.65-7.73 (m, 2H), 7.52 (d, 2H), 7.42 (t, 1H), 6.75 (s, 1H), 6.57 (m, 2H), 3.87 (s, 3H), 1.21 (s, 9H).

EXAMPLE 27 methyl 4-[1-(3-(1,1-dimethylethyl)phenylsulfonyl)-5-trifluoromethyl-1H-pyrrolo[2,3-b]pyridin-2-ylmethyl]benzoate

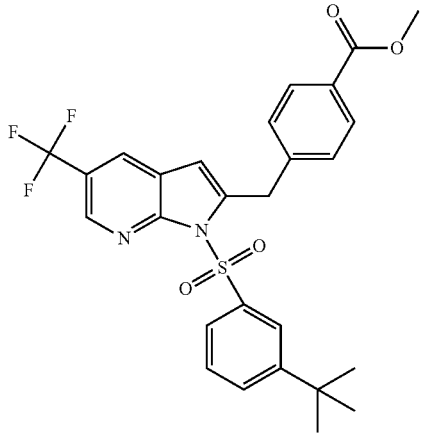 [SMILES: COC(=O)c1ccc(Cc2cc3cc(C(F)(F)F)cnc3n2S(=O)(=O)c2cccc(C(C)(C)C)c2)cc1]

This compound was obtained in the form of a yellow oil by following the procedure described in Example 24, starting with the compound of Example 26 (yield=92%). This compound was used as obtained in the following example.

EXAMPLE 28

4-[[1-[[3-(1,1-dimethylethyl)phenyl]sulfonyl]-5-(trifluoromethyl)-1H-pyrrolo[2,3-b]pyridin-2-yl]methyl]benzoic acid

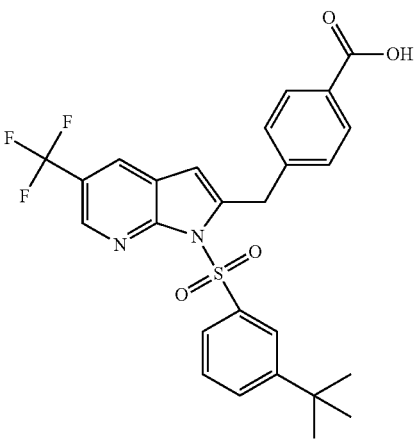 [SMILES: CC(C)(C)c1cccc(S(=O)(=O)n2c(Cc3ccc(C(=O)O)cc3)cc3cc(C(F)(F)F)cnc32)c1]

This compound was obtained in the form of a white solid by following the procedure described in Example 10, starting with the compound of Example 27 (yield=22%). m.p.=209° C.

PREPARATION 21

N-(5-chloro-3-iodopyridin-2-yl)-4-(1-methylethyl)benzene-sulfonamide

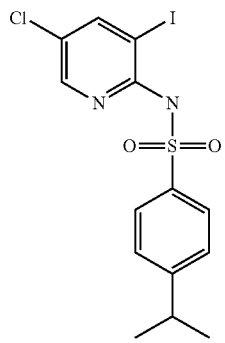 [SMILES: CC(C)c1ccc(S(=O)(=O)Nc2ncc(Cl)cc2I)cc1]

This compound was obtained in the form of an orange solid, by following the procedure described in Preparation 1, starting with 5-chloro-3-iodopyridin-3-ylamine and 4-isopropylbenzenesulfonyl chloride (yield=15%).

¹H NMR (250 MHz, DMSO) δ=10.42 (s, 1H), 8.40 (d, 1H), 8.23 (s, 1H), 7.91 (d, 2H), 7.44 (d, 2H), 2.97 (m, 1H), 1.21 (d, 6H).

EXAMPLE 29 methyl 4-{hydroxy[5-chloro-1-(4-(1-methylethyl)phenylsulfonyl)-1H-pyrrolo[2,3-b]pyridin-2-yl]methyl}benzoate

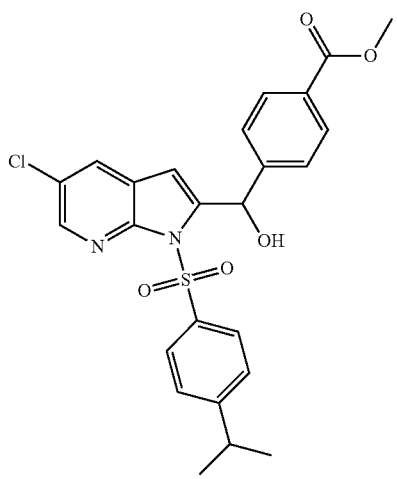 [SMILES: COC(=O)c1ccc(C(O)c2cc3cc(Cl)cnc3n2S(=O)(=O)c2ccc(C(C)C)cc2)cc1]

This compound was obtained in the form of a yellow solid by following the procedure described in Preparation 2, from the compound of Preparation 21 and methyl 4-(1-hydroxyprop-2-ynyl)benzoate (yield=58%). m.p.=77° C.

EXAMPLE 30 methyl 4-[5-chloro-1-(4-(1-methylethyl)phenylsulfonyl)-1H-pyrrolo[2,3-b]pyridin-2-ylmethyl]benzoate

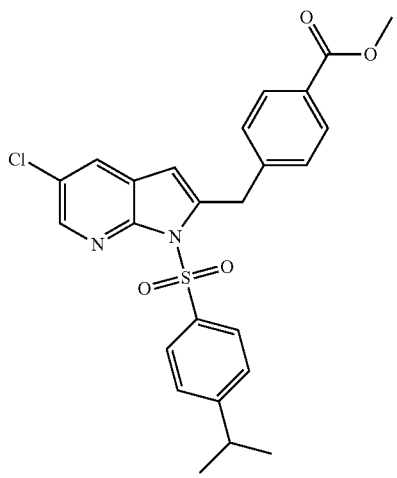 [SMILES: COC(=O)c1ccc(Cc2cc3cc(Cl)cnc3n2S(=O)(=O)c2ccc(C(C)C)cc2)cc1]

This compound was obtained in the form of a beige-coloured solid by following the procedure described in Example 24, starting with the compound of Example 29 (yield=77%). m.p.=186° C.

EXAMPLE 31

4-[[5-chloro-1-[[4-(1-methylethyl)phenyl]sulfonyl]-1H-pyrrolo[2,3-b]pyridin-2-yl]methyl]benzoic acid

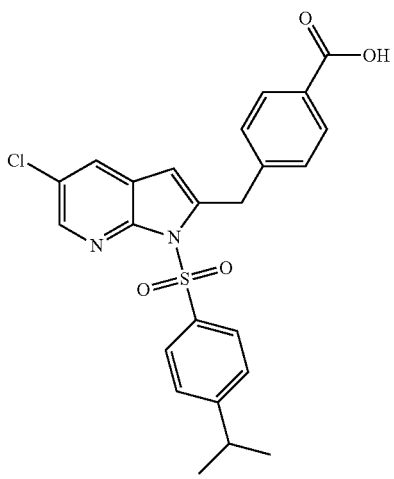 [SMILES: CC(C)c1ccc(S(=O)(=O)n2c(Cc3ccc(C(=O)O)cc3)cc3cc(Cl)cnc32)cc1]

This compound was obtained in the form of a white solid by following the procedure described in Example 10, starting with the compound of Example 30 (yield=100%). m.p.=227° C.

PREPARATION 22

5-(1-hydroxyprop-2-ynyl)thiophene-2-carboxylic acid

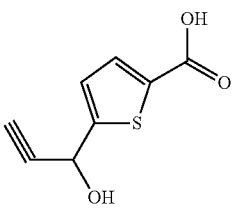

A solution of 2.342 g (15.0 mM) of 5-formyl-2-thiophenecarboxylic acid in 23.4 mL of distilled THF was prepared. 60.0 mL of a solution of ethylmagnesium bromide (0.50 mol/l; 30.0 mM) were added dropwise. The medium was stirred at room temperature for two hours. It was then poured into a mixture of 200 mL of ice and 70 mL of 1 M HCl and extracted with 100 mL of DCM and then twice 50 mL. The organic phases were dried over magnesium sulfate and combined, and then concentrated under reduced pressure. The title product was obtained in the form of a beige-coloured solid (2.6 g, yield=100%). m.p.=128° C.

EXAMPLE 32

5-{hydroxy[1-(3-(1,1-dimethylethyl)phenylsulfonyl)-5-trifluoromethyl-1H-pyrrolo[3,2-b]pyridin-2-yl]methyl}thiophene-2-carboxylic acid

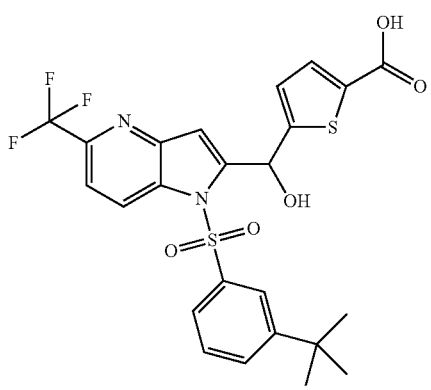 [SMILES: CC(C)(C)c1cccc(S(=O)(=O)n2c(C(O)c3ccc(C(=O)O)s3)cc3nc(C(F)(F)F)ccc32)c1]

This compound was obtained in the form of a white solid by following the procedure described in Preparation 2, from the compound of Preparation 1 and Preparation 22 (yield=5%). m.p.=100° C.

EXAMPLE 33

5-[[1-[[3-(1,1-dimethylethyl)phenyl]sulfonyl]-5-(trifluoromethyl)-1H-pyrrolo[3,2-b]pyridin-2-yl]fluoromethyl]-N,N-diethyl-2-thiophenecarboxamide

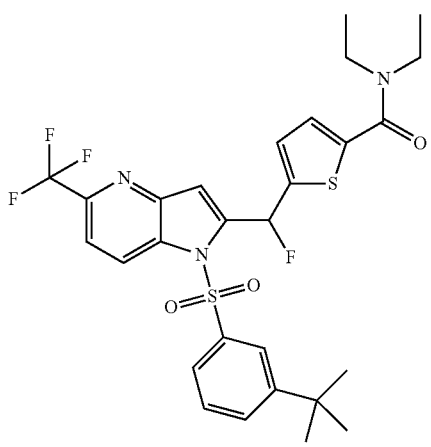 [SMILES: CCN(CC)C(=O)c1ccc(C(F)c2cc3nc(C(F)(F)F)ccc3n2S(=O)(=O)c2cccc(C(C)(C)C)c2)s1]

A solution of 160 mg (0.30 mM) of 5-{hydroxy[1-(3-(1,1-dimethylethyl)-phenylsulfonyl)-5-trifluoromethyl-1H-pyrrolo[3,2-b]pyridin-2-yl]methyl}thiophene-2-carboxylic acid (Example 32) in 10 mL of DCM was prepared. 238.55 µl of (n-Bu)₃N (1.0 mM) were added and the medium was then stirred for 5 minutes. The solvent and the excess reagent were evaporated off. The amorphous solid obtained was redissolved in 10 mL of DCM. This solution was cooled to −78° C. under an argon atmosphere. 238.75 µl of DAST (1.78 mM) were added dropwise. The medium was stirred for 1 hour at −78° C., and was then allowed to warm to room temperature and was stirred for a further 1 hour. 100 mL of sodium carbonate solution were added, followed by 40 mL of 10 M HCl solution, and the mixture was extracted with 100 mL of DCM and then twice with 50 mL. The organic phases were combined and dried over magnesium sulfate, and the solvent was evaporated off. The evaporation residue was purified by semi-preparative LC-MS liquid chromatography (on a SunFire® C18 column) eluting with a water/acetonitrile mixture. The fractions containing the expected product were combined and concentrated to dryness. The title product was obtained in the form of a brown solid (19.85 mg, yield=11%).

¹H NMR (500 MHz, DMSO) δ=8.75 (d, 1H), 7.93 (d, 1H), 7.81 (t, 1H), 7.76 (d, 1H), 7.72 (d, 1H), 7.69 (d, 1H), 7.49 (t, 1H), 7.32 (dd, 2H), 7.30 (d, 1H), 3.46 (broad s, 4H), 1.18 (m, 15H).

EXAMPLE 34

5-{1-(3-(1,1-dimethylethyl)phenylsulfonyl)-5-trifluoromethyl-1H-pyrrolo[3,2-b]pyridine-2-carbonyl}thiophene-2-carboxylic acid

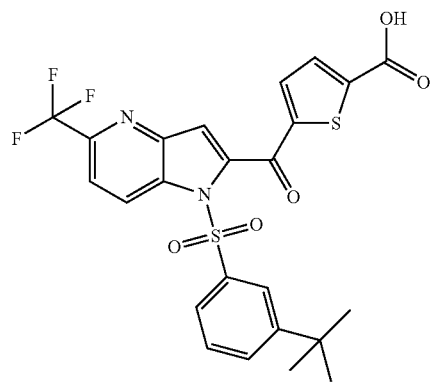 [SMILES: CC(C)(C)c1cccc(S(=O)(=O)n2c(C(=O)c3ccc(C(=O)O)s3)cc3nc(C(F)(F)F)ccc32)c1]

A solution of 110.00 mg (0.20 mM) of 5-{hydroxy[1-(3-(1,1-dimethyl-ethyl)phenylsulfonyl)-5-trifluoromethyl-1H-pyrrolo[3,2-b]pyridin-2-yl]methyl}thiophene-2-carboxylic acid (Example 32) in 5 mL of acetonitrile and 5 mL of water was prepared. 260.95 mg (1.84 mM) of sodium hydrogen phosphate were added. The medium was stirred for 15 minutes at room temperature. 110.83 mg of sodium chlorite (1.22 mM), 0.24 mL (13.0 g/1; 0.04 mM) of a sodium hypochlorite solution and 3.19 mg of 2,2,6,6-tetramethylpiperidine-1-oxyl (0.02 mM) were added. The medium was stirred for 5 hours at room temperature. 25 mL of 10% thiosulfate solution, 50 mL of water and 25 mL of M HCl were added and the mixture was then extracted four times with 50 mL of DCM. The organic phases were combined and dried over magnesium sulfate, and the solvent was evaporated off. The evaporation residue was purified by semi-preparative LC-MS liquid chromatography (on a SunFire® C18 column) eluting with a water/acetonitrile mixture. The fractions containing the expected product were combined and concentrated to dryness. The title product was obtained in the form of a white solid (12 mg, yield=11%). m.p.=108° C.

EXAMPLE 35

4-[[5-chloro-1-[[4-(1-methylethyl)phenyl]sulfonyl]-1H-pyrrolo[2,3-b]pyridin-2-yl]methyl]benzoic acid, sodium salt

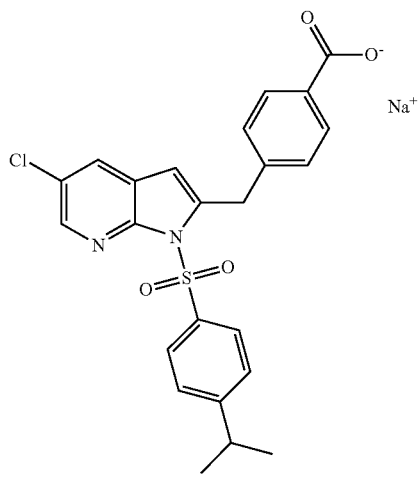 [SMILES: CC(C)c1ccc(S(=O)(=O)n2c(Cc3ccc(C(=O)[O-])cc3)cc3cc(Cl)cnc32)cc1 ; [Na+]]

A solution of 50 mg (0.11 mM) of 4-[[5-chloro-1-[[4-(1-methylethyl)-phenyl]sulfonyl]-1H-pyrrolo[2,3-b]pyridin-2-yl]methyl]benzoic acid (Example 31) in 2.5 mL of THF was prepared. 0.21 mL of sodium hydroxide (0.50 mol/l; 0.11 mM) was added. The reaction medium was stirred overnight at room temperature and then evaporated under vacuum to obtain 31 mg of sodium salt in the form of a white solid (yield=63%). m.p.=218° C.

$^1$H NMR (400 MHz, DMSO) δ=8.32 (d, 1H), 8.05 (d, 1H), 7.82 (d, 2H), 7.79 (d, 2H), 7.36 (d, 2H), 7.15 (d, 2H), 6.30 (s, 1H), 4.47 (s, 2H), 2.91 (m, 1H), 1.15 (d, 6H).

EXAMPLE 36

4-[[5-chloro-1-[[4-(1-methylethyl)phenyl]sulfonyl]-1H-pyrrolo[2,3-b]pyridin-2-yl]methyl]benzoic acid, piperazine salt

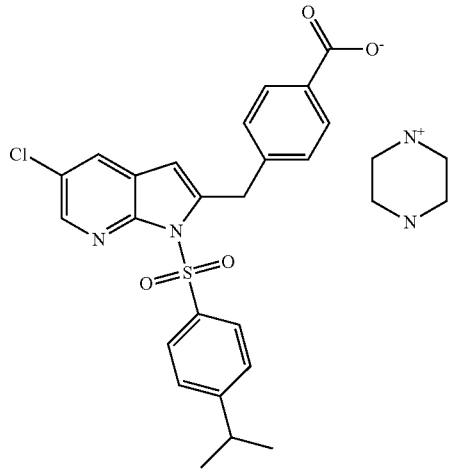 [SMILES: CC(C)c1ccc(S(=O)(=O)n2c(Cc3ccc(C(=O)[O-])cc3)cc3cc(Cl)cnc32)cc1 ; C1C[NH2+]CCN1]

A solution of 46.20 mg (0.10 mM) of 4-[[5-chloro-1-[[4-(1-methylethyl)-phenyl]sulfonyl]-1H-pyrrolo[2,3-b]pyridin-2-yl]methyl]benzoic acid (Example 31) in 4 mL of THF was prepared. 8.49 mg of piperazine (0.10 mM) were added. The reaction medium was stirred for 24 hours at room temperature and then evaporated under vacuum to obtain 40 mg of piperazine salt in the form of a white solid (yield=80%). m.p.=105° C.

$^1$H NMR (400 MHz, DMSO) δ=8.34 (d, 1H), 8.08 (d, 1H), 7.86 (d, 2H), 7.79 (d, 2H), 7.36 (d, 2H), 7.27 (d, 2H), 6.37 (s, 1H), 4.53 (s, 2H), 2.91 (m, 1H), 2.79 (s, 8H), 1.14 (d, 6H).

PREPARATION 23

1-(3-(1,1-dimethylethyl)phenylsulfonyl)-2,3-dimethyl-5-trifluoro-methyl-1H-pyrrolo[3,2-b]pyridine

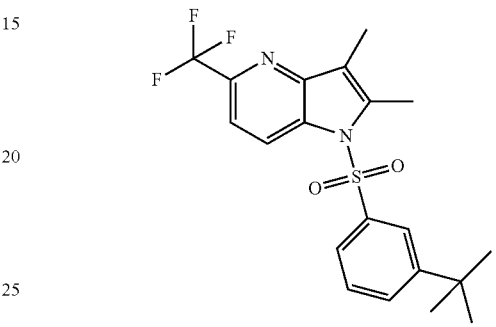

A solution of 242.14 mg (0.50 mM) of the compound of Preparation 1 in 10 mL of DMF was prepared. 11.22 mg (0.04 mM) of palladium acetate, 21.20 mg (0.50 mM) of anhydrous lithium chloride, 345.51 mg (2.50 mM) of potassium carbonate and then 135.23 mg (2.5 mM) of 2-butyne were added. The medium was irradiated with microwaves for 30 minutes at 100° C. 100 mL of water were added. The resulting mixture was extracted with four times 100 mL of DCM and then with four times 100 mL of ethyl acetate. The organic phases were dried over magnesium sulfate. The medium was concentrated under reduced pressure and the evaporation residue was purified by chromatography on silica gel using 95/5 (v/v) cyclohexane/ethyl acetate as eluent. 220 mg of title product were obtained in the form of a yellow oil (yield=91.5%).

$^1$H NMR (300 MHz, DMSO) δ=8.66 (d, 1H), 7.81 (d, 1H), 7.77 (m, 2H), 7.69 (dt, 1H), 7.53 (t, 1H), 2.61 (s, 3H), 2.18 (s, 3H), 1.21 (s, 9H).

EXAMPLE 37

4-[[1-[[3-(1,1-dimethylethyl)phenyl]sulfonyl]-3-methyl-5-(trifluoro-methyl)-1H-pyrrolo[3,2-b]pyridin-2-yl]methyl]benzoic acid

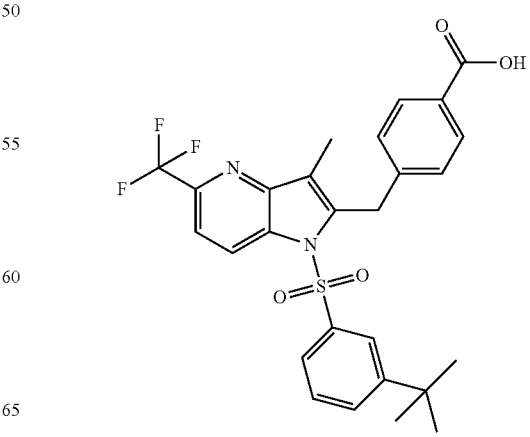

A solution of 310.0 mg (0.76 mM) of 1-(3-(1,1-dimethylethyl)phenylsulfonyl)-2,3-dimethyl-5-trifluoromethyl-1H-pyrrolo[3,2-b]pyridine (Preparation 23) in 5 mL of carbon tetrachloride was prepared. 180.0 mg (1.01 mM) of N-bromosuccinimide (NBS) were added and the medium was then brought to reflux. 12.40 mg (0.08 mM) of azobisisobutyronitrile (AIBN) were then added and the medium was then stirred at reflux for 24 hours. A degree of conversion of 50% was observed. A further 200.00 mg (1.12 mM) of NBS and then 24.8 mg (0.16 mM) of AIBN were added and stirring at reflux was continued for 24 hours. 25 mL of DCM were added to the medium and the solvents were evaporated off. The evaporation residue was purified by chromatography on silica gel using 95/5 (v/v) cyclohexane/ethyl acetate as eluent, to give 435 mg of 2-bromomethyl-1-(3-(1,1-dimethylethyl)phenylsulfonyl)-3-methyl-5-trifluoromethyl-1H-pyrrolo[3,2-b]pyridine in the form of an orange solid (purity=58%).

A solution of 200.0 mg (0.41 mM) of the preceding compound in a mixture of 10 mL of dimethyl ether (DME) and 2 mL of water was prepared. 33.38 mg (0.04 mM) of 1,1'-bis(diphenylphosphino)ferrocenepalladium(II) dichlorure-dichloromethane complex, 101.73 mg (0.61 mM) of 4-carboxyphenylboronic acid and 399.50 mg (1.23 mM) of caesium carbonate were added. The medium was stirred at reflux for 2 hours. 100 mL of water and 100 mL of M HCl were added and the resulting mixture was extracted with four times 100 mL of DCM. The organic phases were dried over magnesium sulfate and the solvent was evaporated off. The evaporation residue was purified by semi-preparative LC-MS liquid chromatography (on a Discovery® column), eluting with a water/acetonitrile/TFA mixture. The fractions containing the expected product were combined and concentrated to dryness. The target product was obtained in the form of a beige-coloured solid (20 mg, yield=9.6%).

PREPARATION 24

[1-(4-(1,1-methylethyl)phenylsulfonyl)-5-chloro-1H-pyrrolo[2,3-b]pyridin-2-yl]methanol

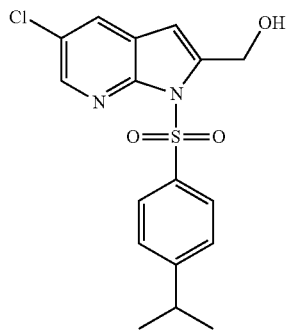 [SMILES: CC(C)c1ccc(S(=O)(=O)n2c(CO)cc3cc(Cl)cnc32)cc1]

This compound was obtained in the form of a beige-coloured solid by following the procedure described in Preparation 2, from the compound of Preparation 21 and 2-propyn-1-ol (yield=78%). m.p.=140° C.

PREPARATION 25

2-bromomethyl-[1-(4-(1,1-methylethyl)phenylsulfonyl)-5-chloro-1H-pyrrolo[2,3-b]pyridine

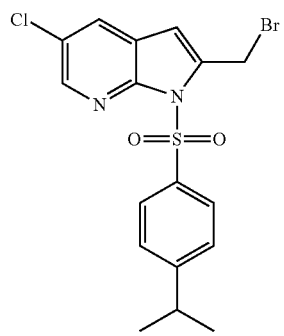 [SMILES: CC(C)c1ccc(S(=O)(=O)n2c(CBr)cc3cc(Cl)cnc32)cc1]

This compound was obtained in the form of a white solid from the compound of Preparation 24, by following the procedure described in Preparation 3 (yield=65%). m.p.=138° C.

EXAMPLE 38

5-[[1-[[4-(1,1-methylethyl)phenyl]sulfonyl]-5-chloro-1H-pyrrolo[2,3-b]pyridin-2-yl]methyl]thiophene-2-carboxylic acid

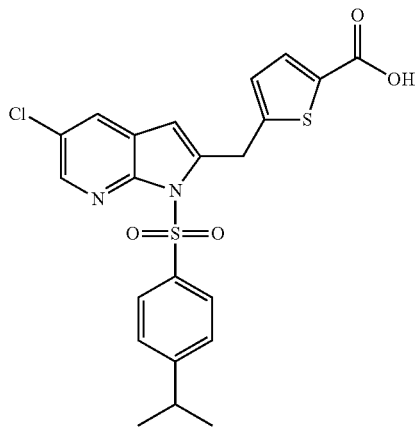 [SMILES: CC(C)c1ccc(S(=O)(=O)n2c(Cc3ccc(C(=O)O)s3)cc3cc(Cl)cnc32)cc1]

This compound was obtained in the form of a beige-coloured solid by following the procedure described in Example 1, from the compound of Preparation 25 and 5-(dihydroxyboryl)-2-thiophenecarboxylic acid (yield=3%). m.p.=210-243° C.

EXAMPLE 39

N-{4-[1-(3-tert-butylbenzenesulfonyl)-5-trifluoromethyl-1H-pyrrolo[3,2-b]pyridin-2-ylmethyl]benzoyl}methanesulfonamide

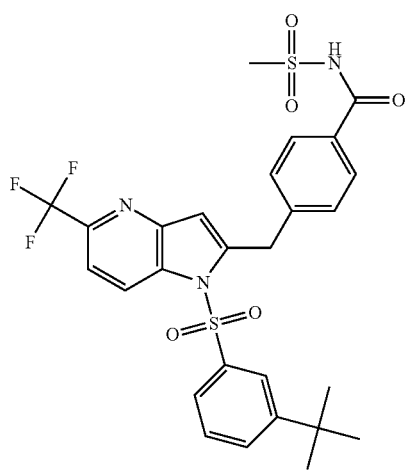 [SMILES: CC(C)(C)c1cccc(S(=O)(=O)n2c(Cc3ccc(C(=O)NS(C)(=O)=O)cc3)cc3nc(C(F)(F)F)ccc32)c1]

A solution of 240 mg (0.46 mM) of the compound of Example 22 in 12 mL of dichloromethane was prepared. 89.07 mg (0.46 mM) of 1-ethyl-3-(3-dimethylaminopropyl) carbodiimide (EDCI), 56.76 mg (0.46 mM) of 4-dimethylaminopyridine and 88.839 mg (0.93 mM) of methanesulfonamide were added. The reaction medium was stirred for 20 hours at room temperature. It was then concentrated under reduced pressure and the evaporation residue was purified by preparative liquid chromatography (LC-MS), eluting with an $H_2O/CH_3CN/0.1\%$ TFA mixture. The fractions containing the expected product were combined and concentrated under reduced pressure to give the desired product in the form of a white solid (yield: 39%). m.p.=95° C.

Pharmacological Activity

The compounds of the invention underwent biological tests so as to evaluate their potential for treating or preventing certain neurodegenerative pathologies.

The ability of the compounds according to the invention to behave as activators of the heterodimers formed by the NURR-1 nuclear receptor and the RXR nuclear receptors was measured, by means of an in vitro test.

A transactivation test was used as a primary screening test. Cos-7 cells were co-transfected with a plasmid expressing a construct of the NURR-1-Gal4 human receptor, a plasmid expressing the RXR human receptor (RXRα or RXRγ receptor) and a reporter plasmid 5Gal4pGL3-TK-Luc. The transfections were performed using a chemical agent (Jet PEI).

The transfected cells were distributed into 384-well plates and left to stand for 24 hours.

After 24 hours, the culture medium was changed. The test products were added (final concentration of between $10^{-4}$ and $3\times10^{-10}$ M) in the culture medium. After incubating overnight, the luciferase expression was measured after addition of "SteadyGlo" according to the manufacturer's instructions (Promega).

4-[[6-Methyl-2-phenyl-5-(2-propenyl)-4-pyrimidinyl]amino]benzoic acid (reference XCT0135908, described by Wallen-Mackenzie et al. 2003, Genes & Development 17: 3036-3047) at $2\times10^{-5}$ M (RXR agonist) was used as reference.

The levels of induction were calculated relative to the basal activity of each heterodimer. The results were expressed as a percentage of the level of induction relative to the level of induction obtained with the reference (the level of induction of the reference is arbitrarily equal to 100%).

By way of example, among the compounds according to the invention, the following results are obtained expressed as a percentage relative to a reference activator compound NURR-1/RXR(XCT0135908):

| | hNurr1_RXRγFL | | hNurr1_RXRαFL | |
|---|---|---|---|---|
| Example | $EC_{50}$ (nM) | Eff (%) | $EC_{50}$ (nM) | Eff (%) |
| 1 | 73 | 64 | 25 | 67 |
| 2 | 100 | 86 | 52 | 70 |
| 4 | — | — | 35 | 104 |
| 5 | — | — | 2344 | 94 |
| 6 | — | — | 17 | 137 |
| 7 | — | — | 11 | 119 |
| 8 | 1514 | 72 | 1023 | 103 |
| 10 | 576 | 82 | 337 | 68 |
| 12 | 761 | 75 | 310 | 81 |
| 14 | 771 | 54 | 541 | 64 |
| 16 | 1052 | 53 | 575 | 68 |
| 18 | 495 | 69 | 194 | 62 |
| 20 | 1189 | 27 | 731 | 42 |
| 22 | 93 | 68 | 42 | 92 |
| 25 | nc | 52 | nc | 57 |
| 28 | 803 | 51 | 634 | 66 |
| 31 | 1346 | 48 | 713 | 63 |
| 32 | — | — | 288 | 84 |
| 33 | — | — | 1820 | 92 |
| 34 | — | — | 1000 | 31 |
| 35 | — | — | 481 | 61 |
| 36 | — | — | 361 | 71 |
| 37 | — | — | 146 | 67 |
| 38 | — | — | 295 | 80 |
| 39 | — | — | 269 | 51 |

—: not tested
nc: not calculable
Eff: percentage efficacy relative to the reference XCT0135908

The compounds according to the invention show a level of induction that is up to 137% (NURR1/RXRα) and 86% (NURR1/RXRγ☐☐) and $EC_{50}$ values that are up to 11 nM (NURR1/RXRα) and 73 nM (NURR1/RXRγ☐☐).

These in vitro results show that the compounds of the invention are capable of modifying the mechanisms of the disease on certain cell models, and of stopping the degenerative process by generating neuroprotective agents that can combat the cell death of dopaminergic neurons. They therefore confirm the advantage of these compounds for their use as active principles of medicaments for preventing and/or treating neurodegenerative diseases and more particularly Parkinson's disease.

The invention also relates to a pharmaceutical composition containing, as active principle, at least one compound of formula (I), or a pharmaceutically acceptable salt thereof.

According to another aspect, the present patent application is directed towards covering the use of a compound of formula (I) or of a pharmaceutical composition containing such a compound, for the prevention and/or treatment of diseases in which the NURR-1 receptor is involved, especially neurodegenerative diseases and more particularly Parkinson's disease.

According to another aspect, the present patent application is directed towards covering a method for preventing and/or treating diseases in which the NURR-1 receptor is involved, especially neurodegenerative diseases and more particularly Parkinson's disease, which consists in administering to a patient in need thereof a therapeutically effective amount of a compound of formula (I) or a pharmaceutical composition containing such a compound.

The pharmaceutical compositions in accordance with the invention may be prepared conventionally, using pharmaceutically acceptable excipients, in order to obtain forms for parenteral or, preferably, oral administration, for example tablets or gel capsules.

In the case of injectable forms, the compounds of formula (I) will advantageously be used in the form of soluble salts in an aqueous medium. As indicated previously, the salts are preferentially formed between a compound of formula (I) and a pharmaceutically acceptable non-toxic base. The formulation may be either a solution of the compound in an isotonic aqueous medium in the presence of soluble excipients, or a lyophilizate of the compound to which the dilution solvent is extemporaneously added. These preparations may be injected in perfusion form or as a bolus, as a function of the patient's requirements.

In practice, in the case of parenteral administration of the compound, the daily dosage in man will preferably be between 2 and 250 mg.

The preparations for oral administration will preferably be in the form of a gel capsule or a tablet containing the finely ground or better still micronized compound of the invention, and mixed with excipients known to those skilled in the art, for instance lactose, pregelatinized starch and magnesium stearate.

By way of example, a mixture formed from 500 g of the finely ground compound of Example 2, 500 g of pregelatinized starch, 1250 g of lactose, 15 g of sodium lauryl sulfate and 235 g of polyvinylpyrrolidone was granulated. This granulated mixture was then added to 20 g of magnesium stearate and 80 g of microcrystalline cellulose, and the mixture obtained was divided, after milling and screening, into 260-mg gel capsules. Gel capsules each containing 50 mg of active principle were thus obtained.

In practice, in the case of oral administration of the compound, the daily dosage in man will preferably be between 5 and 500 mg. To this effect, unit doses comprising from 5 to 250 mg of active principle and preferably unit doses comprising from 5 to 100 mg of active principle may be used.

The invention claimed is:

1. A compound corresponding to formula (I):

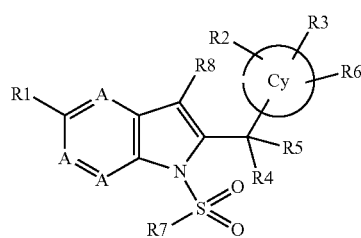

(I)

wherein:
one of the groups A represents a nitrogen atom and the other groups A represent a carbon atom;
Cy represents a phenyl or a 5- or 6-membered heteroaromatic ring;
R1 represents a hydrogen atom, a halogen atom, a group $(C_1-C_4)$alkyl that is optionally totally or partially halogenated, or a group $(C_1-C_4)$alkoxy;
R2 and R3 represent, independently of each other, a hydrogen atom, a halogen atom, a group $(C_1-C_4)$alkyl, a hydroxyl group or a group $(C_1-C_4)$alkoxy;
R4 and R5 represent, independently of each other, a hydrogen atom, a halogen atom, a group $(C_1-C_4)$alkyl or a hydroxyl group; or
R4 and R5 form, together with the carbon atoms to which they are attached, an ethylene group (C=CH2) or a carbonyl group (C=O);
R6 represents a group —COOR9 or a group —SO$_2$NHR10, —CONHNH—COOR11, —CONR12R13 or —CONHSO$_2$R14, or a group

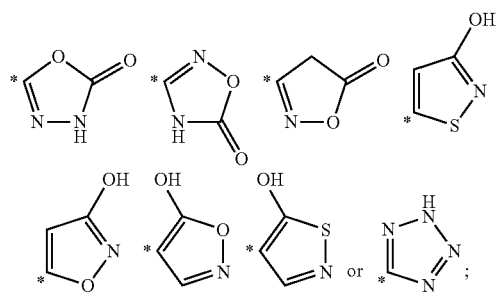

R7 represents a phenyl optionally substituted with a group $(C_1-C_4)$alkyl, or a 6- to 10-membered heteroaromatic ring optionally substituted with a group $(C_1-C_4)$alkyl;
R8 represents a hydrogen atom, a group $(C_1-C_4)$alkyl or a halogen atom;
R9 represents a hydrogen atom or a group $(C_1-C_4)$alkyl;
R10, R11, R12, R13 and R14 represent, independently of each other, a hydrogen atom or a group $(C_1-C_4)$alkyl;
or a pharmaceutically acceptable salt of the compound of formula (I);
with the exception of the following compounds:
2-(1-phenylsulfonyl-1H-pyrrolo[2,3-b]pyridin-2-yl-carbonyl)benzoic acid;
N,N-diethyl-4-[hydroxy[1-(phenylsulfonyl)-1H-pyrrolo[2,3-b]pyridin-2-yl]methyl]-2-methoxy-3-pyridinecarboxamide;
N,N-diethyl-2-methoxy-4-[[1-(phenylsulfonyl)-1H-pyrrolo[2,3-b]pyridin-2-yl]carbonyl]-3-pyridinecarboxamide;
N,N-diethyl-4-[1-hydroxy-1-[1-(phenylsulfonyl)-1H-pyrrolo[2,3-b]pyridin-2-yl]ethyl]-2-methoxy-3-pyridinecarboxamide.

2. A compound according to claim 1, wherein R8 represents a hydrogen atom;
or a pharmaceutically acceptable salt of such a compound.

3. A compound according to claim 1, wherein:
Cy represents a phenyl or a 5- or 6-membered heteroaromatic ring;
R1 represents a halogen atom or a group $(C_1-C_4)$alkyl that is optionally totally or partially halogenated;
R2 and R3 represent, independently of each other, a hydrogen atom or a halogen atom;
R4 and R5 represent, independently of each other, a hydrogen atom, a halogen atom or a hydroxyl group; or
R4 and R5 form, together with the carbon atom to which they are attached, a carbonyl group (C=O);
R6 represents a group —COOR9;
R7 represents a phenyl optionally substituted with a group $(C_1-C_4)$alkyl;
R8 represents a hydrogen atom;

R9 represents a hydrogen atom or a group (C$_1$-C$_4$)alkyl;
or a pharmaceutically acceptable salt of such a compound.

4. A compound according to claim 1, wherein Cy represents a phenyl, thienyl, thiazolyl, furyl or pyridyl;
or a pharmaceutically acceptable salt of such a compound.

5. A compound according to claim 1, wherein R2 and R3 each represent a hydrogen atom;
or a pharmaceutically acceptable salt of such a compound.

6. A compound according to claim 1, wherein R4 and R5 each represent a hydrogen atom;
or a pharmaceutically acceptable salt of such a compound.

7. A compound according to claim 1, selected from the group consisting of:
- 5-[[1-[[3-(1,1-dimethylethyl)phenyl]sulfonyl]-5-(trifluoromethyl)-1H-pyrrolo[3,2-b]pyridin-2-yl]methyl]-thiophene-2-carboxylic acid,
- 3-[[1-[[3-(1,1-dimethylethyl)phenyl]sulfonyl]-5-(trifluoromethyl)-1H-pyrrolo[2,3-c]pyridin-2-yl]methyl]-2-benzoic acid,
- 2-chloro-4-[[1-[[3-(1,1-dimethylethyl)phenyl]sulfonyl]-5-(trifluoromethyl)-1H-pyrrolo[2,3-c]pyridin-2-yl]methyl]-benzoic acid,
- 5-[[1-[[3-(1,1-dimethylethyl)phenyl]sulfonyl]5-(trifluoromethyl)-1H-pyrrolo[2,3-c]pyridin-2-yl]methyl]-furane-3-carboxylic acid,
- 5-[[1-[[3-(1,1-dimethylethyl)phenyl]sulfonyl]-5-(trifluoromethyl)-1H-pyrrolo[2,3-c]pyridin-2-yl]methyl]-pyridine-3-carboxylic acid,
- 4-[[1-[[3-(1,1-dimethylethyl)phenyl]sulfonyl]-5-(trifluoromethyl)-1H-pyrrolo[2,3-c]pyridin-2-yl]methyl]-thiophene-2-carboxylic acid,
- 5-[[1-[[3-(1,1-dimethylethyl)phenyl]sulfonyl]-5-(trifluoromethyl)-1H-pyrrolo[2,3-c]pyridin-2-yl]methyl]-2-fluoro-benzoic acid,
- 2-[[1-[[3-(1,1-dimethylethyl)phenyl]sulfonyl]-5-(trifluoromethyl)-1H-pyrrolo[3,2-b]pyridin-2-yl]methyl]-thiazole-4-carboxylic acid,
- Methyl 4-[1-(4-(1-methylethyl)phenylsulfonyl)-5-trifluoromethyl-1H-pyrrolo[2,3-b]pyridin-2-ylmethyl]-benzoate,
- 4-[[1-[[3-(1-methylethyl)phenyl]sulfonyl]-5-(trifluoromethyl)-1H-pyrrolo[2,3-b]pyridin-2-yl]methyl]-benzoic acid,
- Methyl 4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]-benzoate,
- 4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]-benzoic acid,
- Methyl 4-[1-(4-(1-methylethyl)phenylsulfonyl)-5-trifluoromethyl-1H-pyrrolo[2,3-c]pyridin-2-ylmethyl]-benzoate,
- 4-[[1-[[4-(1-methylethyl)phenyl]sulfonyl]-5-(trifluoromethyl)-1H-pyrrolo[2, 3 -c]pyridin-2-yl]methyl]-benzoic acid,
- Methyl 4-[1-(4-(1-methylethyl)phenylsulfonyl)-5-trifluoromethyl-1H-pyrrolo[3,2-b]pyridin-2-ylmethyl]-benzoate,
- 4-[1-(4-(1-methylethyl)phenylsulfonyl)-5-trifluoromethyl-1H-pyrrolo[3,2-b]pyridin-2-ylmethyl]-benzoic acid,
- Methyl 4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]-benzoate,
- 4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]-benzoic acid,
- Methyl 4-[1-(4-(1-methylethyl)phenylsulfonyl)-5-chloro-1H-pyrrolo[2,3-c]pyridin-2-ylmethyl]-benzoate,
- 4-[[5-chloro-1-[[4-(1-methylethyl)phenyl]sulfonyl]-1H-pyrrolo[2,3-c]pyridin-2-yl]methyl]-benzoic acid,
- Methyl 4-[1-(3-(1,1-dimethylethyl)phenylsulfonyl)-5-trifluoromethyl-1H-pyrrolo[3,2-b]pyridin-2-ylmethyl]-benzoate,
- 4-[[1-[[3-(1,1-dimethylethyl)phenyl]sulfonyl]-5-(trifluoromethyl)-1H-pyrrolo[3,2-b]pyridin-2-yl]methyl]-benzoic acid,
- Methyl 4-{Hydroxy-[1-(3-(1-methylethyl)phenylsulfonyl)-5-trifluoromethyl-1H-pyrrolo[2,3-b]pyridin-2-yl]-methyl}-benzoate,
- Methyl 4-[1-(3-(1-methylethyl)phenylsulfonyl)-5-trifluoromethyl-1H-pyrrolo[2,3-b]pyridin-2-ylmethyl]-benzoate,
- 4-[[1-[[3-(1-methylethyl)phenyl]sulfonyl]-5-(trifluoromethyl)-1H-pyrrolo[2,3-b]pyridin-2-yl]methyl]-benzoic acid,
- Methyl 4-{Hydroxy-[1-(3-(1,1-dimethylethyl)phenylsulfonyl)-5-trifluoromethyl-1H-pyrrolo[2,3-b]pyridin-2-yl]-methyl}-benzoate,
- Methyl 4-[1-(3-(1,1-dimethylethyl)phenylsulfonyl)-5-trifluoromethyl-1H-pyrrolo[2,3-b]pyridin-2-ylmethyl]-benzoate,
- 4-[[1-[[3-(1,1-dimethylethyl)phenyl]sulfonyl]-5-(trifluoromethyl)-1H-pyrrolo[2,3-b]pyridin-2-yl]methyl]-benzoic acid,
- Methyl 4-{Hydroxy-[5-chloro-1-(4-(1-methylethyl)phenylsulfonyl)-1H-pyrrolo[2,3-b]pyridin-2-yl]-methyl}-benzoate,
- Methyl 4-[5-Chloro-1-(4-(1-methylethyl)phenylsulfonyl)-1H-pyrrolo[2,3-b]pyridin-2-ylmethyl]-benzoate,
- 4-[[5-chloro-1-[[4-(1-methylethyl)phenyl]sulfonyl]-1H-pyrrolo-[2,3-b]pyridin-2-yl]methyl]benzoic acid,
- 5-{hydroxy[1-(3-(1,1-dimethylethyl)phenylsulfonyl)-5-trifluoromethyl-1H-pyrrolo[3,2-b]pyridin-2-yl]methyl}thiophene-2-carboxylic acid,
- 5-[[1-[[3-(1,1-dimethylethyl)phenyl]sulfonyl]-5-(trifluoromethyl)-1H-pyrrolo[3,2-b]pyridin-2-yl]fluoromethyl]-N,N-diethyl-2-thiophenecarboxamide,
- 5-{1-(3-(1,1-dimethylethyl)phenylsulfonyl)-5-trifluoromethyl-1H-pyrrolo[3,2-b]pyridine-2-carbonyl}thiophene-2-carboxylic acid,
- 4-[[5-chloro-1-[[4-(1-methylethyl)phenyl]sulfonyl]-1H-pyrrolo[2,3-b]pyridin-2-yl]methyl]benzoic acid, sodium salt,
- 4-[[5-chloro-1-[[4-(1-methylethyl)phenyl]sulfonyl]-1H-pyrrolo[2,3-b]pyridin-2-yl]methyl]benzoic acid, piperazine salt,
- 4-[[1-[[3-(1,1-dimethylethyl)phenyl]sulfonyl]-3-methyl-5-(trifluoromethyl)-1H-pyrrolo[3,2-b]pyridin-2-yl]methyl]benzoic acid,
- 5-[[1-[[4-(1,1-methylethyl)phenyl]sulfonyl]-5-chloro-1H-pyrrolo[2,3-b]pyridin-2-yllmethyl]thiophene-2-carboxylic acid,
- N-{4-[1-(3-tert-butylbenzenesulfonyl)-5-trifluoromethyl-1H-pyrrolo[3,2-b]pyridin-2-ylmethylThenzoyl}methanesulfonamide; and pharmaceutically acceptable salts of any of the foregoing compounds.

8. A method of treating Parkinson's disease by agonizing the NURR-1 nuclear receptors which comprises administering to a subject in need thereof a therapeutically effective amount of a compound of formula (I) . . . "

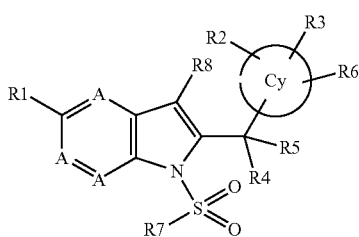

(I)

wherein:
one of the groups A represents a nitrogen atom and the other groups A represent a carbon atom;
Cy represents a phenyl or a 5- or 6-membered heteroaromatic ring;
R1 represents a hydrogen atom, a halogen atom, a group $(C_1-C_4)$alkyl that is optionally totally or partially halogenated, or a group $(C_1-C_4)$alkoxy;
R2 and R3 represent, independently of each other, a hydrogen atom, a halogen atom, a group $(C_1-C_4)$alkyl, a hydroxyl group or a group $(C_1-C_4)$alkoxy;
R4 and R5 represent, independently of each other, a hydrogen atom, a halogen atom, a group $(C_1-C_4)$alkyl or a hydroxyl group; or
R4 and R5 form, together with the carbon atoms to which they are attached, an ethylene group (C=CH2) or a carbonyl group (C=O);
R6 represents a group —COOR9 or a group —SO2NHR10, —CONHNH—COOR11, —CONR12R13 or —CONHSO2R14, or a group

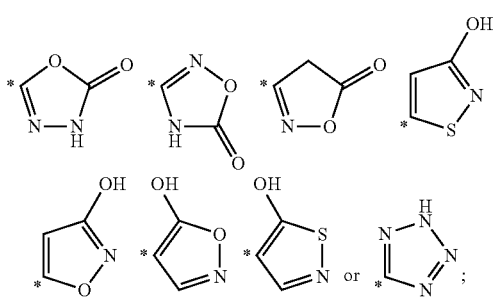

R7 represents a phenyl optionally substituted with a group $(C_1-C_4)$alkyl, or a 6- to 10-membered heteroaromatic ring optionally substituted with a group $(C_1-C_4)$alkyl;
R8 represents a hydrogen atom, a group $(C_1-C_4)$alkyl or a halogen atom;
R9 represents a hydrogen atom or a group $(C_1-C_4)$alkyl;
R10, R11, R12, R13 and R14 represent, independently of each other, a hydrogen atom or a group $(C_1-C_4)$alkyl;
or a pharmaceutically acceptable salt thereof.

9. A method according to claim 8, wherein in the formula (I) compound R8 represents a hydrogen atom.

10. A method according to claim 8, wherein in the formula (I) compound:
Cy represents a phenyl or a 5- or 6-membered heteroaromatic ring;
R1 represents a halogen atom or a group $(C_1-C_4)$alkyl that is optionally totally or partially halogenated;
R2 and R3 represent, independently of each other, a hydrogen atom or a halogen atom;
R4 and R5 represent, independently of each other, a hydrogen atom, a halogen atom or a hydroxyl group; or R4 and R5 form, together with the carbon atom to which they are attached, a carbonyl group (C=O);
R6 represents a group —COOR9;
R7 represents a phenyl optionally substituted with a group $(C_1-C_4)$alkyl;
R8 represents a hydrogen atom;
R9 represents a hydrogen atom or a group $(C_1-C_4)$alkyl.

11. A method according to claim 8, wherein in the formula (I) compound Cy represents a phenyl, thienyl, thiazolyl, furyl or pyridyl.

12. A method according to claim 8, wherein in the formula (I) compound R2 and R3 each represent a hydrogen atom.

13. A method according to claim 8, wherein in the formula (I) compound R4 and R5 each represent a hydrogen atom.

14. A method according to claim 8, wherein the formula (I) compound is selected from the group consisting of:
5-[[1-[[3-(1,1-dimethylethyl)phenyl]sulfonyl]-5-(trifluoromethyl)-1H-pyrrolo[3,2-b]pyridin-2-yl]methyl]-thiophene-2-carboxylic acid,
3-[[1-[[3-(1,1-dimethylethyl)phenyl]sulfonyl]-5-(trifluoromethyl)-1H-pyrrolo[2,3-c]pyridin-2-yl]methyl]-2-benzoic acid,
2-chloro-4-[[1-[[3-(1,1-dimethylethyl)phenyl]sulfonyl]-5-(trifluoromethyl)-1H-pyrrolo[2,3-c]pyridin-2-yl]methyl]-benzoic acid,
5-[[1-[[3-(1,1-dimethylethyl)phenyl]sulfonyl]-5-(trifluoromethyl)-1H-pyrrolo[2,3-c]pyridin-2-yl]methyl]-furane-3-carboxylic acid,
5-[[1-[[3-(1,1-dimethylethyl)phenyl]sulfonyl]-5-(trifluoromethyl)-1H-pyrrolo[2,3-c]pyridin-2-yl]methyl]-pyridine-3-carboxylic acid,
4-[[1-[[3-(1,1-dimethylethyl)phenyl]sulfonyl]-5-(trifluoromethyl)-1H-pyrrolo[2,3-c]pyridin-2-yl]methyl]-thiophene-2-carboxylic acid,
5-[[1-[[3-(1,1-dimethylethyl)phenyl]sulfonyl]-5-(trifluoromethyl)-1H-pyrrolo[2,3-c]pyridin-2-yl]methyl]-2-fluoro-benzoic acid,
2-[[1-[[3-(1,1-dimethylethyl)phenyl]sulfonyl]-5-(trifluoromethyl)-1H-pyrrolo[3,2-b]pyridin-2-yl]methyl]-thiazole-4-carboxylic acid,
Methyl 4-[1-(4-(1-methylethyl)phenylsulfonyl)-5-trifluoromethyl-1H-pyrrolo[2,3-b]pyridin-2-ylmethyl]-benzoate,
4-[[1-[[3-(1-methylethyl)phenyl]sulfonyl]-5-(trifluoromethyl)-1H-pyrrolo[2,3-b]pyridin-2-yl]methyl]-benzoic acid,
Methyl 4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]-benzoate,
4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]-benzoic acid,
Methyl 4-[1-(4-(1-methylethyl)phenylsulfonyl)-5-trifluoromethyl-1H-pyrrolo[2,3-c]pyridin-2-ylmethyl]-benzoate,
4-[[1-[[4-(1-methylethyl)phenyl]sulfonyl]-5-(trifluoromethyl)-1H-pyrrolo[2,3-c]pyridin-2-yl]methyl]benzoic acid,
Methyl 4-[1-(4-(1-methylethyl)phenylsulfonyl)-5-trifluoromethyl-1H-pyrrolo[3,2-b]pyridin-2-ylmethyl]-benzoate, 4-[1-(4-(1-methylethyl)phenylsulfonyl)-5-trifluoromethyl-1H-pyrrolo[3,2-b]pyridin-2-ylmethyl]-benzoic acid, Methyl 4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]-benzoate, 4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]-benzoic acid, Methyl 4-[1-(4-(1-methylethyl)phenylsulfonyl)-5-chloro-1H-pyrrolo[2,3-c]pyridin-2-ylmethyl]-benzoate, 4-[[5-chloro-1-[[4-(1-methylethyl)phenyl]sulfonyl]-1H-pyrrolo[2,3-c]pyridin-2-yl]methyl]-benzoic acid, Methyl 4-[1-(3-(1,1-dimethylethyl)phenylsulfonyl)-5-trifluoromethyl-1H-pyrrolo[3,2-b]pyridin-2-ylmethyl]-benzoate, 4-[[1-[[3-(1,1-dimethylethyl)phenyl]sulfonyl]-5-(trifluoromethyl)-1H-pyrrolo[3,2-b]pyridin-2-yl]methyl]-benzoic acid, Methyl 4-{Hydroxy-[1-(3-(1-methylethyl)phenylsulfonyl)-5-trifluoromethyl-1H-pyrrolo[2,3-b]pyridin-2-yl]-methyl}-benzoate, Methyl 4-[1-(3-(1-methylethyl)phenylsulfonyl)-5-trifluoromethyl-1H-pyrrolo[2,3-b]pyridin-2-ylmethyl]-benzoate, 4-[[1-[[3-(1-methylethyl)phenyl]sulfonyl]-5-(trifluoromethyl)-1H-pyrrolo[2,3-b]pyridin-2-yl]methyl]benzoic acid, Methyl 4-{Hydroxy-[1-(3-(1,1-dimethylethyl)phenylsulfonyl)-5-trifluoromethyl-1H-pyrrolo[2,3-b]pyridin-2-yl]-methyl}-benzoate, Methyl 4-[1-(3-(1,1-dimethylethyl)phenylsulfonyl)-5-trifluoromethyl-1H-pyrrolo[2,3-b]pyridin-2-ylmethyl]-benzoate, 4-[[1-[[3-(1,1-dimethylethyl)phenyl]sulfonyl]-5-(trifluoromethyl)-1H-pyrrolo[2,3-b]pyridin-2-yl]methyl]-benzoic acid, Methyl 4-{Hydroxy-[5-chloro-1-(4-(1-methylethyl)phenylsulfonyl)-1H-pyrrolo[2,3-b]pyridin-2-yl]-methyl}-benzoate, Methyl 4-[5-Chloro-1-(4-(1-methylethyl)phenylsulfonyl)-1H-pyrrolo[2,3-b]pyridin-2-ylmethyl]-benzoate, 4-[[5-chloro-1-[[4-(1-methylethyl)phenyl]sulfonyl]-1H-pyrrolo-[2,3-b]pyridin-2-yl]methyl]benzoic acid, 5-{hydroxy[1-(3-(1,1-dimethylethyl)phenylsulfonyl)-5-trifluoromethyl-1H-pyrrolo[3,2-b]pyridin-2-yl]methyl}thiophene-2-carboxylic acid, 5-[[1-[[3-(1,1-dimethylethyl)phenyl]sulfonyl]-5-(trifluoromethyl)-1H-pyrrolo[3,2-b]pyridin-2-yl]fluoromethyl]-N,N-diethyl-2-thiophenecarboxamide, 5-{1-(3-(1,1-dimethylethyl)phenylsulfonyl)-5-trifluoromethyl-1H-pyrrolo[3,2-b]pyridine-2-carbonyl}thiophene-2-carboxylic acid, 4-[[5-chloro-1-[[4-(1-methylethyl)phenyl]sulfonyl]-1H-pyrrolo[2,3-b]pyridin-2-yl]methyl]benzoic acid, sodium salt, 4-[[5-chloro-1-[[4-(1-methylethyl)phenyl]sulfonyl]-1H-pyrrolo[2,3-b]pyridin-2-yl]methyl]benzoic acid, piperazine salt, 4-[[1-[[3-(1,1-dimethylethyl)phenyl]sulfonyl]-3-methyl-5-(trifluoromethyl)-1H-pyrrolo[3,2-b]pyridin-2-yl]methylbenzoic acid, 5-[[1-[[4-(1,1-methylethyl)phenyl]sulfonyl]-5-chloro-1H-pyrrolo[2,3-b]pyridin-2-yl]methyl]thiophene-2-carboxylic acid, N-{4-[1-(3-tert-butylbenzenesulfonyl)-5-trffluoromethyl-1H-pyrrolo[3,2-b]pyridin-2-ylmethyl]benzoyl}methanesulfonamide; and pharmaceutically acceptable salts of these compounds.

15. A pharmaceutical composition comprising (i) a compound of formula (I) or a pharmaceutically acceptable salt thereof and (ii) at least one pharmaceutically acceptable excipient:

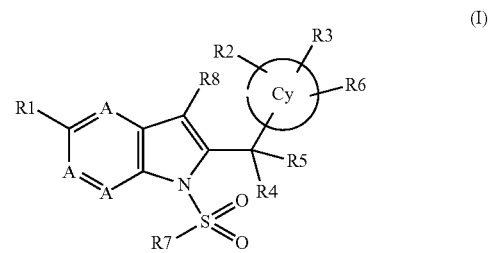

wherein:
one of the groups A represents a nitrogen atom and the other groups A represent a carbon atom;
Cy represents a phenyl or a 5- or 6-membered heteroaromatic ring;
R1 represents a hydrogen atom, a halogen atom, a group $(C_1-C_4)$alkyl that is optionally totally or partially halogenated, or a group $(C_1-C_4)$alkoxy;
R2 and R3 represent, independently of each other, a hydrogen atom, a halogen atom, a group $(C_1-C_4)$alkyl, a hydroxyl group or a group $(C_1-C_4)$alkoxy;
R4 and R5 represent, independently of each other, a hydrogen atom, a halogen atom, a group $(C_1-C_4)$alkyl or a hydroxyl group; or R4 and R5 form, together with the carbon atoms to which they are attached, an ethylene group (C=CH2) or a carbonyl group (C=O);
R6 represents a group —COOR9 or a group —SO2NHR10, —CONHNH—COOR11, —CONR12R13 or —CONHSO2R14, or a group

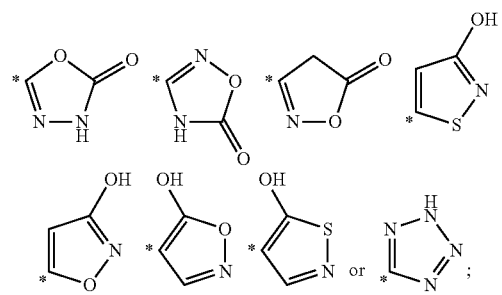

R7 represents a phenyl optionally substituted with a group $(C_1-C_4)$alkyl, or a 6- to 10-membered heteroaromatic ring optionally substituted with a group $(C_1-C_4)$alkyl;
R8 represents a hydrogen atom, a group $(C_1-C_4)$alkyl or a halogen atom;
R9 represents a hydrogen atom or a group $(C_1-C_4)$alkyl;
R10, R11, R12, R13 and R14 represent, independently of each other, a hydrogen atom or a group $(C_1-C_4)$alkyl;

or a pharmaceutically acceptable salt thereof.

16. A pharmaceutical composition according to claim 15, wherein in the formula (I) compound R8 represents a hydrogen atom.

17. A pharmaceutical composition according to claim 15, wherein in the formula (I) compound:
Cy represents a phenyl or a 5- or 6-membered heteroaromatic ring;
R1 represents a halogen atom or a group $(C_1-C_4)$alkyl that is optionally totally or partially halogenated;
R2 and R3 represent, independently of each other, a hydrogen atom or a halogen atom;
R4 and R5 represent, independently of each other, a hydrogen atom, a halogen atom or a hydroxyl group; or R4 and R5 form, together with the carbon atom to which they are attached, a carbonyl group (C=O);
R6 represents a group —COOR9;
R7 represents a phenyl optionally substituted with a group $(C_1-C_4)$alkyl;
R8 represents a hydrogen atom;
R9 represents a hydrogen atom or a group $(C_1-C_4)$alkyl.

18. A pharmaceutical composition according to claim 15, wherein in the formula (I) compound Cy represents a phenyl, thienyl, thiazolyl, furyl or pyridyl.

19. A pharmaceutical composition according to claim 15, wherein in the formula (I) compound R2 and R3 each represent a hydrogen atom.

20. A pharmaceutical composition according to claim 15, wherein in the formula (I) compound R4 and R5 each represent a hydrogen atom.

21. A pharmaceutical composition according to claim 15, wherein the formula (I) compound is selected from the group consisting of:

5-[[1-[[3-(1,1-dimethylethyl)phenyl]sulfonyl]-5-(trifluoromethyl)-1H-pyrrolo[3,2-b]pyridin-2-yl]methyl]-thiophene-2-carboxylic acid,
3-[[1-[[3-(1,1-dimethylethyl)phenyl]sulfonyl]-5-(trifluoromethyl)-1H-pyrrolo[2,3-c]pyridin-2-yl]methyl]-2-benzoic acid,
2-chloro -4-[[1-[[3-(1,1-dimethylethyl)phenyl]sulfonyl]-5-(trifluoromethyl)-1H-pyrrolo[2,3-c]pyridin-2-yl]methyl]-benzoic acid,
5-[[1-[[3-(1,1-dimethylethyl)phenyl]sulfonyl]-5-(trifluoromethyl)-1H-pyrrolo[2,3-c]pyridin-2-yl]methyl]-furane-3-carboxylic acid,
5-[[1-[[3-(1,1-dimethylethyl)phenyl]sulfonyl]-5-(trifluoromethyl)-1H-pyrrolo[2,3-c]pyridin-2-yl]methyl]-pyridine-3-carboxylic acid,
4-[[1-[[3-(1,1-dimethylethyl)phenyl]sulfonyl]-5-(trifluoromethyl)-1H-pyrrolo[2,3-c]pyridin-2-yl]methyl]-thiophene-2-carboxylic acid,
5-[[1-[[3-(1,1-dimethylethyl)phenyl]sulfonyl]-5-(trifluoromethyl)-1H-pyrrolo[2,3-c]pyridin-2-yl]methyl]-2-fluoro-benzoic acid,
2-[[1-[[3-(1,1-dimethylethyl)phenyl]sulfonyl]-5-(trifluoromethyl)-1H-pyrrolo[3,2-b]pyridin-2-yl]methyl]-thiazole-4-carboxylic acid,
Methyl 4-[1-(4-(1-methylethyl)phenylsulfonyl)-5-trifluoromethyl-1H-pyrrolo[2, 3-b]pyridin-2-ylmethyl]-benzoate,
4-[[1-[[3-(1-methylethyl)phenyl]sulfonyl]-5-(trifluoromethyl)-1H-pyrrolo[2,3-b]pyridin-2-yl]methyl]-benzoic acid,
Methyl 4-[[1-[(3,4-dihydro-4-methyl-2H-1,4-benzoxazin-6-yl)sulfonyl]-5-(trifluoromethyl)-1H-pyrrolo[2, 3-c]pyridin-2-yl]methyl]-benzoate,
4-[[1-[(3,4-dihydro-4-methyl-2H-1,4-benzoxazin-6-yl)sulfonyl]-5-(trifluoromethyl)-1H-pyrrolo[2,3-c]pyridin-2-yl]methyl]-benzoic acid,
Methyl 4-[1-(4-(1-methylethyl)phenylsulfonyl)-5-trifluoromethyl-1H-pyrrolo[2,3-c]pyridin-2-ylmethyl]-benzoate,
4-[[1-[[4-(1-methylethyl)phenyl]sulfonyl]-5-(trifluoromethyl)-1H-pyrrolo[2,3-c]pyridin-2-yl]methyl]-benzoic acid,
Methyl 4-[1-(4-(1-methylethyl)phenylsulfonyl)-5-trifluoromethyl-1H-pyrrolo[3,2-b]pyridin-2-ylmethyl]-benzoate,
4-[1-(4-(1-methylethyl)phenylsulfonyl)-5-trifluoromethyl-1H-pyrrolo[3,2-b]pyridin-2-ylmethyl]benzoic acid,
Methyl 4-[[1-[(3,4-dihydro-4-methyl-2H-1,4-benzoxazin-6-yl)sulfonyl]-5-(trifluoromethyl)-1H-pyrrolo[2, 3-b]pyridin-2-yl]methyl]-benzoate,
4-[[1-[(3,4-dihydro-4-methyl-2H-1,4-benzoxazin-6-yl)sulfonyl]-5-(trifluoromethyl)-1H-pyrrolo[2,3-b]pyridin-2-yl]methyl]-benzoic acid,
Methyl 4-[1-(4-(1-methylethyl)phenylsulfonyl)-5-chloro-1H-pyrrolo[2,3-c]pyridin-2-ylmethyl] -benzoate,
4-[[5-chloro-1-[[4-(1-methylethyl)phenyl]sulfonyl]-1H-pyrrolo[2,3-c]pyridin-2-yl]methyl]benzoic acid,
Methyl 4-[1-(3-(1,1-dimethylethyl)phenylsulfonyl)-5-trifluoromethyl-1H-pyrrolo[3,2-b]pyridin-2-ylmethyl]-benzoate,
4-[[1-[[3-(1,1-dimethylethyl)phenyl]sulfonyl]-5-(trifluoromethyl)-1H-pyrrolo[3,2-b]pyridin-2-yl]methyl]-benzoic acid,
Methyl 4-{Hydroxy-[1-(3-(1-methylethyl)phenylsulfonyl)-5-trifluoromethyl-1H-pyrrolo[2,3-b]pyridin-2-yl]-methyl}-benzoate,
Methyl 4-[1-(3-(1-methylethyl)phenylsulfonyl)-5-trifluoromethyl-1H-pyrrolo[2,3-b]pyridin-2-ylmethyl]-benzoate,
4-[[1-[[3-(1-methylethyl)phenyl]sulfonyl]-5-(trifluoromethyl)-1H-pyrrolo[2,3-b]pyridin-2-yl]methyl]-benzoic acid,
Methyl 4-{Hydroxy-[1-(3-(1,1-dimethylethyl)phenylsulfonyl)-5-trifluoromethyl-1H-pyrrolo[2,3-b]pyridin-2-yl]-methyl}-benzoate,
Methyl 4-[1-(3-(1,1-dimethylethyl)phenylsulfonyl)-5-trifluoromethyl-1H-pyrrolo[2,3-b]pyridin-2-ylmethyl]-benzoate,
4-[[1-[[3-(1,1-dimethylethyl)phonyl]sulfonyl]-5-(trifluoromethyl)-1H-pyrrolo[2,3-b]pyridin-2-yl]methyl]-benzoic acid,
Methyl 4-{Hydroxy-[5-chloro-1-(4-(1-methylethyl)phenylsulfonyl)-1H-pyrrolo[2,3-b]pyridin-2-yl]-methyl]-benzoate,
Methyl 4-[5-Chloro-1-(4-(1-methylethyl)phenylsulfonyl)-1H-pyrrolo[2,3-b]pyridin-2-ylmethyl]-benzoate,
4-[[5-chloro-1-[[4-(1-methylethyl)phenyl]sulfonyl]-1H-pyrrolo-[2,3-b]pyridin-2-yl]methyl]-benzoic acid,
5-{hydroxy[1-(3-(1,1-dimethylethyl)phenylsulfonyl)-5-trifluoromethyl-1H-pyrrolo[3,2-b]pyridin-2-yl]methyl}thiophene-2-carboxylic acid,
5-[[1-[[3-(1,1-dimethylethyl)phenyl]sulfonyl]-5-(trifluoromethyl)-1H-pyrrolo[3,2-b]pyridin-2-yl]fluoromethyl]-N,N-diethyl-2-thiophenecarboxamide,
5-{1-(3-(1,1-dimethylethyl)phenylsulfonyl)-5-trifluoromethyl-1H-pyrrolo[3,2-b]pyridine-2-carbonyl}thiophene-2-carboxylic acid,
4-[[5-chloro-1-[[4-(1-methylethyl)phenyl]sulfonyl]-1H-pyrrolo[2,3-b]pyridin-2-yl]methyl]benzoic acid, sodium salt, 4-[[5-chloro-1-[[4-(1-methylethyl)phenyl]sulfonyl]-1H-pyrrolo[2,3-b]pyridin-2-yl]methyl]benzoic acid, piperazine salt, 4-[[1-[[3-(1,1-dimethylethyl)phenyl]sulfonyl]-3-methyl-5-(trifluoromethyl)-1H-pyrrolo[3, 2-b]pyridin-2-yl]methyl]benzoic acid, 5-[[1-[[4-(1,1-methylethyl)phenyl]sulfonyl]-5-chloro-1H-pyrrolo[2,3-b]pyridin-2-yl]methyl]thiophene-2-carboxylic acid, N-{4-[1-(3-tert-butylbenzenesulfonyl)-5-trifluoromethyl-1H-pyrrolo[3,2-b]pyridin-2-ylmethyl]benzoyl}methanesulfonamide; and pharmaceutically acceptable salts of these compounds.

* * * * *